US007238514B2

(12) United States Patent
Matsuda et al.

(10) Patent No.: US 7,238,514 B2
(45) Date of Patent: Jul. 3, 2007

(54) DITERPENE-PRODUCING UNICELLULAR ORGANISM

(75) Inventors: Seiichi P. T. Matsuda, Houston, TX (US); Elizabeth A. Hart, Houston, TX (US)

(73) Assignee: William Marsh Rice University, Houston, TX (US)

(*) Notice: Subject to any disclaimer, the term of this patent is extended or adjusted under 35 U.S.C. 154(b) by 298 days.

(21) Appl. No.: 10/041,018

(22) Filed: Jan. 7, 2002

(65) Prior Publication Data

US 2004/0072323 A1   Apr. 15, 2004

Related U.S. Application Data

(60) Provisional application No. 60/259,880, filed on Jan. 5, 2001.

(51) Int. Cl.
  C12N 1/20    (2006.01)
  C12N 1/14    (2006.01)
  C12N 1/00    (2006.01)
  C12N 15/00   (2006.01)
  C12N 9/10    (2006.01)
  C12N 9/88    (2006.01)
  C12P 1/00    (2006.01)
  C12P 21/06   (2006.01)
  C07K 1/00    (2006.01)
  C07H 21/04   (2006.01)

(52) U.S. Cl. .................. 435/252.3; 435/193; 435/232; 435/320.1; 435/325; 435/254.2; 435/254.21; 435/69.1; 435/41; 530/350; 536/23.2

(58) Field of Classification Search ................ 435/193, 435/232, 320.1, 325, 252.3, 252.21, 69.1, 435/41, 254.21, 254.2; 530/350; 536/23.2
See application file for complete search history.

(56) References Cited

U.S. PATENT DOCUMENTS

| | | | |
|---|---|---|---|
| 4,849,410 A | 7/1989 | Jacobs et al. ................ 514/33 |
| 5,151,352 A | 9/1992 | Nakano et al. .............. 435/123 |
| 5,189,187 A | 2/1993 | Nakano et al. .............. 549/548 |
| 5,241,084 A | 8/1993 | Teng ........................... 549/297 |
| 5,322,688 A | 6/1994 | Schwabe ................. 424/195.1 |
| 5,389,370 A | 2/1995 | O'Reilly et al. ......... 424/195.1 |
| 5,399,348 A | 3/1995 | Schwabe ................. 424/195.1 |
| 5,429,939 A | 7/1995 | Misawa et al. ............... 435/67 |
| 5,473,057 A | 12/1995 | Fenical et al. ............. 536/17.3 |
| 5,512,286 A | 4/1996 | Schwabe ................. 424/195.1 |
| 5,589,581 A | 12/1996 | Misawa et al. ............ 536/23.2 |
| 5,599,950 A | 2/1997 | Teng ........................... 549/297 |
| 5,602,184 A | 2/1997 | Myers et al. ................ 514/739 |
| 5,637,302 A | 6/1997 | Bombardelli et al. .... 424/195.1 |
| 5,637,484 A | 6/1997 | Yukimune et al. ........... 435/123 |
| 5,968,789 A | 10/1999 | Yukimune et al. ........... 435/123 |
| 6,235,287 B1 | 5/2001 | Weidner et al. .......... 424/195.1 |
| 6,531,303 B1 | 3/2003 | Millis et al. ................ 435/155 |
| 6,689,593 B2 | 2/2004 | Millis et al. ................ 435/155 |
| 2003/0148479 A1 | 8/2003 | Keasling et al. ............ 435/131 |
| 2004/0005678 A1 | 1/2004 | Keasling et al. ............ 435/146 |

OTHER PUBLICATIONS

Witkowski et al., Biochemistry 38:11643-11650, 1999.*
Seffernick et al., J. Bacteriol. 183(8):2405-2410, 2001.*
Broun et al., Science 282:1315-1317, 1998.*
Richman et al., The Plant Journal 19(4):411-421, 1999.*
Branden et al., Introduction to Protein Structure, Garland Publishing Inc., New York, p. 247, 1991.*
Albrecht, M., et al., *Synthesis of atypical cyclic and acyclic hydroxy carotenoids in Escherichia coli transformants*, Journal of Biotechnology 58 177-185, Sep. 22, 1997.
Bailey, James E., *Toward a Science of Metabolic Engineering*, Science, New Series, vol. 252, Issue 5013, 1668-1675, Jun. 21, 1991.
Basson, Michael E., et al., *Identifying Mutations in Duplicated Functions in Saccharomyces cerevisiae: Recessive Mutations in HMG-CoA Reductase Genes*, Genetics, 117, 645-655, Dec. 1987.
Basson, Michael E, *Saccharomyces cerevisiae contains two functional genes encoding 3-hydroxy-3-methylglutaryl-coenzyme A reductase*, Proc. Natl. Acad. Sci. USA 83: 5563-57, 1986.
Corey, E.J., et al., *Isolation of an Arabidopsis thaliana gene encoding cycloartenol synthase by functional expression in a yest mutant lacking lanosterol synthase by the use of a chromatographic screen*, Proc. Natl. Acad. Sci USA vol. 90, pp. 11628-11632, Dec. 1993.
Crowley, James H., et al., *A Mutation in a Purported Regulatory Gene Affects Control of Sterol Uptake in Saccharomyces cerevisiae*, Journal of Bacteriology, vol. 180, No. 16, p. 4177-4183, Aug. 1998.
Funk, Christoph, et al., *Diterpenoid Resin Acis Biosynthesis in Conifers: Characterization of Two Cytochrome P450-Dependent Monooxygenases and an Aldehyde Dehydrogenase Involved in Abietic Acid Biosynthesis*, Archives of Biochemistry and Biophysics, vol. 308, No. 1, pp. 258-266, Jan. 1994.
Hara, Mitsunobu, et al., *Leinamycin, A New Antitumor Antibiotic From Streptomyces, Producing Organism, Fermentation and Isolation*, The Journal of Antibiotics, pp. 1768-1774, Dec. 1989.
Hezari, Mehri, et al., *Purification and Characterization of Taxa-4(5), 11(12)-diene Synthase from Pacific Yew (Taxus brevifolia) that Catalyzes the First Committed Step of Taxol Biosynthesis*, Archives of Biochemistry and Biophisics, vol. 322, No. 2, pp. 437-444, Oct. 1, 1995.
Jiang, Yu, et al., *BTSI Encodes a Geranylgeranyl Diphosphate Synthase in Saccharomyces cerevisiae*, The Journal of Biological Chemistry, vol. 270, No. 37, pp. 21793-21799, Sep. 15, 1995.
Kajiwara, Susumu, et al., *Expression of an exogenous isopentenyl diphosphate isomerase gene enhances isoprenoid biosynthesis in Escherichia coli*, Biochem J., 324(Pt 2): 421-6, Jun. 1, 1997.

(Continued)

*Primary Examiner*—Delia M. Ramirez
(74) *Attorney, Agent, or Firm*—Baker Botts L.L.P.

(57) ABSTRACT

The present invention is directed to a unicellular organism system, such as a yeast, for producing geranylgeranyl pyrophosphate and a diterpene in vivo. The yeast cell preferably comprises an inducible nucleic acid sequence encoding geranylgeranyl pyrophosphate synthase, an inducible nucleic acid sequence encoding a soluble form of HMG-CoA reductase, a nucleic acid sequence of an allele that confers an increase in sterol metabolic flux and, in the diterpene-producing cell, a diterpene synthase.

69 Claims, 9 Drawing Sheets

OTHER PUBLICATIONS

Kholodenko, Boris N., et al., *Metabolic Design: How to Engineer a Living Cell to Desired Metabolite Concentrations and Fluxes*, Biotechnol Bioeng, 59(2):239-247, Jul. 20, 1998.

LaFever, Roy E., et al., *Diterpenoid Resin Acis Biosynthesis in Conifers: Enzymatic Cyclization of Geranylgeranyl Pyrophosphate to Abietadiene, the Precursor of Abietic Acid*, Archives of Biochemistry and Biophysics, vol. 313. No. 1, pp. 139-149, 1994, Aug. 15, 1994.

Leak, Frank W., et al., *In Yeast, upc2-1 Confers a Decrease in Tolerance to LiCl and NaCl, Which Can Be Suppressed by the P-Type ATPase Encoded by ENA2*, DNA and Cell Biology, vol. 18, No. 2, 1999 pp. 133-139, 1999.

Learned, R. Marc, et al., *3-Hydroxy-3-methylglutaryl-coenzyme A reductase from Arabidopsis thaliana is structurally distinct from the yeast and anmal enzymes*, Proc. Natl. Acad. Sci. USA vol. 86, pp. 2779-2783, Apr. 1989.

Lewis, T.L., et al., *Pleiotropic Mutations in Saccharomyces cerevisiae Affecting Sterol Uptake and Metabolism*, Yeast 4(2):93-106, 1988.

Liu, Shuang-Jiang, et al., *A Novel Genetically Engineered Pathway for Synthesis of Poly (Hydroxyalkanoic Acids) in Escherichia coli*, Applied and Environmental Microbiology, vol. 66. No. 2, p. 739-743, Feb. 2000.

Misawa, Norihiko, et al., *Production of B-Caroltene in Zymomonas mobilis and Agrobacterium tumefaciens by Introduction of the Biosynthesis Genes from Erwinia uredovora*, Applied and Environmental Microbiology, vol. 57, No. 6, p. 1847-1849, Jun. 1991.

Misawa, Norihiko, et al., *Metabolic engineering for the production of carotenoids in non-carotenogenci bacteria and yeasts*, Journal of Biotechnology 59 (1998) 169-181, 1998.

Misawa, Norihiko, et al., *Expression of a Tomato cDNA Coding for Phytoene Synthase in Escherchia coli, Phytoene Formation In Vivo and In Vitro, and Functional Analysis of the Various Truncated Gene Products*, J. Biochem, 116, 980-985 (1994).

Miura, Yutaka, et al., *Production of Lycopene by the Food Yeast, Candida utilis That Does Not Naturally Synthesize Cartenoid*, Biotechnol Bioeng., 58(2-3): 306-8, Apr. 20, 1998.

Miura, Yutaka, et al., *Production of the Carotenoids Lycopene, B-Caroltene, and Astazanthin in the Food Yeast Candida utilis*, Applied and Environmental Microbiology, vol. 64, No. 4, p. 1226-1229, Apr. 1998.

Ness, Frederique, et al., *SUT1 is a putative Zn[II]2Cys6-transcription factor whose upregulation enhances both sterol uptake and synthesis in aerobically growing Saccharomyces cerevisiae cells*, Eur. J. Biochem. 268, 1585-1595, Feb. 2001.

Parks, Leo W., et al., *Physiological Implications of Sterol Biosynthesis in Yeast*, Annu. Rev. Microbiol. 49:95-116, 1995.

Parks, Leo W., et al., *Biochemical and Physiological Effects of Sterol Alternations in Yeast-A Review*, Lipids vol. 30 No. 3:227-230, 1995.

Peters, Reuben J., et al., *Abietadiene Synthase from Grand Fir (Abies grandis) Characterization and Mechanisms of Action of the "Pseudomature" Recombinant Enzyme*, Biochemistry 39: 15592-15602, Dec. 2000.

Polakowski, T., et al., *Overexpression of a cytosolic hydroxymethylglutaryl-CoA reductase leads to squalene accumulation in yeast*, Appl Microbiol Biotechnol, 49:66-71, 1998.

Ravn, Matthew M., et al., *Stereochemistry of the Cyclization-Rearrangement of (+)-Copalyl Diphosphate to (–)-Abietadiene Catalyzed by Recombinant Abietadiene Synthase from Abies grandis*, Org. Letters Vo. 2, No. 5, p. 573-576, Mar. 2000.

Shimada, Hiroshi, et al., *Increased Carotenoid Production by the Food Yeast Candida utilis through Metabolic Engineering of the Isoprenoid Pathway*, App. and Environ. Microbiology, vol. 64, No. 7, p. 2676-2680, Jul. 1998.

Stephanopoulos, G., *Bioinformatics and Metabolic Engineering*, Metabolic Engineering 2(3): 157-158, 2000.

Stofer Vogel, Brigitte, et al., *Abietadiene Synthase from Grand Fir (Abies grandis) cDNA Isolation, Characterization and Bacterial Expression of a Bifunctional Diterpene Cyclase Involved in Resin Acid Biosynthesis*, J Biological Chemistry, vol. 271, No. 38: 23262-23268, Sep. 20, 1996.

Trapp, Susan C., et al., *Genomic Organization of Plant Terpene Synthases and Molecular Evolutionary Implications*, Genetics, 158(2):811-832, Jun. 2001.

Wang, Chia-Wei, et al., *Engineered Isoprenoid Pathway Enhances Astaxanthin Production in Escherichia coli*, Biotech and Bioeng, vol. 62, No. 2, 235-241, Jan. 20, 1999.

Wildung, Mark R., et al., *A cDNA Clone for Taxadiene Synthase, the Diterpene Cyclase That Catalyzes the Committed Step of Taxol Biosynthesis*, J. of Biological Chem., Vo. 271, No. 16: 9201-9204, Apr. 19, 1996.

Yamano, Shigeyuki, et al., *Metabolic Engineering for Production of B-Carotene and Lycopene in Saccharomyces cerevisiae*, Biosci. Biotech. Biochem., 58(6): 1112-1114, 1994.

Martin, Vincent, et al., "*Engineering a mevalonate pathway in Escherichia coli for production of terpenoids*," Nature Biotechnology, vol. 21, No. 7, pp. 796-802, Jul. 2003.

Keasling, Jay, "*Metabolic engineering of Escherichia coli for terpene production.*" Metabolic Engineering, Feb. 18, 2004.

Keasling, Jay, ""*Degradation of Organophosphate Contaminants Synthesis of Isoprenoids*," Metabolioc Engineering of Microorganisms", Nov. 11, 2000.

Balz, Jean-Pierre et al., *Production of Ginkgolides and Bilobalide by Ginkgo biloba Plants and Tissue Cultures*, Planta Medica 65, pp. 620-626, 1999.

Bohlmann, Jorg et al., *Plant terpenoid synthases: Molecular biology and phylogenetic analysis*, Proc. National Acad. Science USA, vol. 95, pp. 4126-4133, Apr. 1998.

Cartayrade, Alain et al., *Ginkgolide and bilobalide biosynthesis in Ginkgo biloba.I: Sites of synthesis, translocation and accumulation of ginkgolides and bilobalide*, Plant Physiol. Biochem. 13(11), pp. 859-868, 1997.

Corey et al., *Total Synthesis of a C15 Ginkgolide*, (±)—*Bilobalide*, J. Am. Chem. Soc. vol. 109, pp. 7534-7536, 1987.

Corey et al., *Total Synthesis of (±)Ginkgolide B*, J. Am. Chem. Soc. vol. 110, pp. 649-651, 1988.

Corey et al., *Total Synthesis of Ginkgolide A*, Tetrahedron Letters, vol. 29, pp. 3205-3206, 1988.

Le Bars, Pierre L. et al., *A Placebo-Controlled, Double-blind, Randomized Trial of an Extract of Ginkgo Biloba for Dementia*, J. Amer. Med. Assoc., vol. 278, No. 16, pp. 1327-1332, 1997.

Neau, Elisabeth et al., *Ginkgolide and bilobalide biosynthesis in Ginkgo biloba. II: Identification of a possible intermediate compound by using inhibitors of cytochrome P-450-dependent oxygenases*, Plant Physiol. Biochem. 35(11), pp. 869-879, 1997.

Schwarz et al., *Binkgolide Biosynthesis*, Comp. Nat. Prod. Chem. 2, pp. 367-400, 1999.

Sousa et al., *The ARO4 gene of Candida albicans encodes a tyrosine-sensitive DAHP synthase: evolution, functional conservation and phenotype of Aro3p-, Aro4p-deficient mutants*, Microbiology 148 (Pt 5), pp. 1291-1303, 2002.

\* cited by examiner

US 7,238,514 B2

DITERPENE-PRODUCING UNICELLULAR ORGANISM

CROSS REFERENCE TO RELATED APPLICATION

This application claims the benefit of U.S. Provisional Application No. 60/259,880, filed Jan. 5, 2001, and entitled "Diterpene-Producing Unicellular Organism."

FIELD OF THE INVENTION

The present invention is directed to the fields of molecular biology, yeast molecular genetics and organic chemistry. More specifically, the present invention is directed to metabolically engineered yeast which produce diterpenes and diterpene precursors in vivo.

BACKGROUND OF THE INVENTION

Metabolic engineering employs recombinant DNA technology to restructure metabolic networks of microorganisms leading to improved production and yields of natural products (Bailey, 1991) This method alters a synchronous series of transformations, defined as a pathway, to produce metabolites. Such pathway manipulations require an awareness of inherent complex regulation and a comprehensive understanding of the discrete enzymatic transformations involved. Metabolic engineering recently emerged in response to efforts made towards improving cellular function by modifying and/or introducing specific biochemical processes (Stephanopoulos, 1996).

Examples of the utility of metabolic engineering have been described and include a modified *Candida utilis* strain, a diploid yeast, and a modified *E. coli* strain, each altered to produce carotenoids (e.g., tetraterpenes). Miura et al. (1998b) and Yamano et al. (1994) describe the engineering of *Escherichia coli* to produce the tetraterpene lycopene by introducing recombinant *Erwinia uredovora* crtE, crtB and crtI genes.

Miura et al. (1998a) described a *Candida utilis* strain that produces lycopene, β-carotene, and astaxantin via an engineered carotenoid biosynthetic pathway that included recombinant *Erwinia uredovora* crtE, crtB, crtI, crtY, crtZ and crtW genes modified to contain the preferred codon usage for *Candida* and then expressed under the control of constitutive promoters. This strain demonstrated 0.4 mg–1.1 mg lycopene per gram dry weight of cells. Employing a similarly modified *C. utilis* strain comprising recombinant carotenoid biosynthetic genes from *E. uredovora*, Shimada et al. (1998) co-expressed the *C. utilis* HMG-CoA reductase catalytic domain to yield 4.3 mg lycopene/g dry weight of cells. Adding a heterozygous squalene synthase deletion, ERG9, in the same strain effected lycopene production at 7.8 mg lycopene/g dry weight of cells was produced. Wang et al. (1999) engineered *Escherichia coli* to generate geranylgeranyl pyrophosphate by overexpressing concomitantly *E. coli* isopentenyl diphosphate isomerase and *Archaeoglobus fulgidus* GGPP synthase. The cells were further modified to contain the *Agrobacterium aurantiacum* crtBIYZW gene cluster to produce the carotenoid astaxanthin. U.S. Pat. No. 5,589,581, and EP Patent Nos. EP0769551 and EP0393690, are directed to *Erwinia uredovora* DNA sequences which encode enzymes that participate in carotenoid biosynthesis.

U.S. Pat. No. 5,429,939 and EP Patent No. 0769551 are directed to a process for producing geranylgeranyl pyrophosphate by transforming a host with a DNA sequence consisting of an *Erwinia uredovora* enzyme involved in carotenoid biosynthesis and which effects transformation of farnesyl pyrophosphate (FPP) to geranylgeranyl pyrophosphate (GGPP).

Terpenes are compounds derived from isopentenyl pyrophosphate and represent a vast and structurally diverse group of natural products comprising at least 30,000 compounds displaying more than 300 ring systems. Terpenes perform crucial roles in vertebrates and include the retinoids, the geranylgeranyl and farnesyl moiety of prenylated proteins, the coenzymes A, vitamins A, D and E, cholesterol and the steroid hormones. Similarly, terpenoid hormones and pheromones are important in invertebrates. Plants control growth and development using regulatory terpenes including the gibberellins, the brassinosteroids, and abscissic acid. Many plants synthesize defense terpenoids that interfere with biological processes in potential herbivores. Some of these compounds are medicinally useful, such as Taxol, ginkgolide and artemisinin.

One terpene sub-class is the diterpenes. In plants, diterpenes serve as defense toxins, volatile defensive signals, pollinator attractants, and photoprotectants (Bohlmann et al., 1998; McGarvey and Croteau, 1995). In addition to the physiological utility imparted to their host, some diterpenes have exhibited clinical and medicinal relevance, such as the diterpene glycosides found in *Pseudopterogorgia elisabethae* that demonstrate anti-inflammatory activity (Look et al., 1986; Mayer et al., 1998). Generally, commercial diterpene production often begins with extraction from natural sources followed by, if necessary, synthetic manipulation. However, natural sources are limited and commercial-scale total syntheses are usually impractical. Therefore, an alternative source for the efficient and inexpensive production of diterpenes is lacking in the art.

The present invention is directed to providing a terpene, specifically a diterpene, producing system in a unicellular organism. In one embodiment a haploid *S. cerevisiae* strain produces significant yields of diterpene and diterpene precursors and is particularly useful as a production mechanism for these compounds.

SUMMARY OF THE INVENTION

In an embodiment of the present invention there is a unicellular organism for producing a diterpene, comprising an exogenous nucleic acid sequence encoding a GGPP synthase; and an exogenous nucleic acid sequence encoding a diterpene synthase. In a specific embodiment, the nucleic acid encoding the diterpene synthase is SEQ ID NO:361; SEQ ID NO:362; SEQ ID NO:412; SEQ ID NO:363; SEQ ID NO:364; SEQ ID NO:365; SEQ ID NO:366; SEQ ID NO:367; SEQ ID NO:368; SEQ ID NO:369; SEQ ID NO:370; SEQ ID NO:371; SEQ ID NO:372; SEQ ID NO:373; SEQ ID NO:374; SEQ ID NO:375; SEQ ID NO:376; SEQ ID NO:377; SEQ ID NO:378; SEQ ID NO:379; SEQ ID NO:380; SEQ ID NO:381; SEQ ID NO:382 or SEQ ID NO:397.

In another specific embodiment, the GGPP synthase is SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or SEQ ID NO:21.

In another specific embodiment, the expression of the nucleic acid sequence encoding GGPP synthase is regulated by an inducible promoter or a constitutive promoter. In a preferred specific embodiment the inducible promoter is selected from the group consisting of GAL1, CUP1 and MET3. In another preferred specific embodiment, the constitutive promoter is selected from the group consisting of ADH and PGK.

In an additional specific embodiment the expression of the nucleic acid sequence encoding diterpene synthase is regulated by an inducible promoter or a constitutive promoter. In a preferred specific embodiment, the inducible promoter is selected from the group consisting of GAL1, CUP1 and MET3. In another preferred specific embodiment, the constitutive promoter is selected from the group consisting of ADH and PGK.

In another specific embodiment the unicellular organism further comprises an exogenous nucleic acid sequence encoding a soluble form of HMG-CoA reductase under control of a promoter operable in the unicellular organism. In a further specific embodiment, the organism produces a diterpene precursor. In another further specific embodiment, the promoter is an inducible promoter or a constitutive promoter. In a preferred specific embodiment, the inducible promoter is selected from the group consisting of GAL1, CUP1 and MET3. In another preferred specific embodiment, the constitutive promoter is selected from the group consisting of ADH and PGK.

In an additional embodiment the unicellular organism further comprises an exogenous nucleic acid sequence that confers to the organism an increase in sterol metabolic flux as compared to native sterol metabolic flux levels.

In a specific embodiment, the nucleic acid sequence encoding the geranylgeranyl pyrophosphate synthase is present on a chromosome of the unicellular organism.

In further specific embodiments, the unicellular organism is a yeast or a bacteria. In a preferred specific embodiment, the bacteria is *Escherichia coli*. In an additional preferred specific embodiment, the yeast is *Saccharomyces*.

Another embodiment of the present invention is a unicellular organism for producing a diterpene precursor, comprising an exogenous nucleic acid sequence encoding a geranylgeranyl pyrophosphate synthase under the control of an inducible promoter operable in said organism; an exogenous nucleic acid sequence encoding a soluble form of HMG-CoA reductase under control of an inducible promoter operable in said organism and an exogenous nucleic acid sequence that confers to said cell an increase in sterol metabolic flux as compared to native sterol metabolic flux levels. In a specific embodiment, the nucleic acid sequence encoding said geranylgeranyl pyrophosphate synthase is SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or SEQ ID NO:21. In another specific embodiment, the organism is a yeast or a bacteria.

Yet another embodiment is a unicellular organism for producing a diterpene precursor, comprising an exogenous nucleic acid sequence encoding a geranylgeranyl pyrophosphate synthase under the control of an inducible promoter operable in said organism; an exogenous nucleic acid sequence encoding a soluble form of HMG-CoA reductase under control of an inducible promoter operable in said organism and a upc2-1 nucleic acid sequence. In a specific embodiment, the nucleic acid sequence encoding said geranylgeranyl pyrophosphate synthase is SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or SEQ ID NO:21. In another specific embodiment, the organism is a yeast.

One embodiment of the present invention is a unicellular organism for producing a diterpene or diterpene precursor, comprising an exogenous nucleic acid sequence encoding a geranylgeranyl pyrophosphate synthase under the control of an inducible promoter operable in said organism; an exogenous nucleic acid sequence encoding a diterpene synthase under the control of an inducible promoter operable in said organism; an exogenous nucleic acid sequence encoding a soluble form of HMG-CoA reductase under control of an inducible promoter operable in said organism; and a upc2-1 nucleic acid sequence. In a specific embodiment, the nucleic acid sequence encoding a geranylgeranyl pyrophosphate synthase is SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO: SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or SEQ ID NO:21. In another specific embodiment, the nucleic acid sequence encoding said diterpene synthase is SEQ ID NO:361; SEQ ID NO:362; SEQ ID NO:412; SEQ ID NO:363; SEQ ID NO:364; SEQ ID NO:365; SEQ ID NO:366; SEQ ID NO:367; SEQ ID NO:368; SEQ ID NO:369; SEQ ID NO:370; SEQ ID NO:371; SEQ ID NO:372; SEQ ID NO:373; SEQ ID NO:374; SEQ ID NO:375; SEQ ID NO:376; SEQ ID NO:377; SEQ ID NO:378; SEQ ID NO:379; SEQ ID NO:380; SEQ ID NO:381; SEQ ID NO:382 or SEQ ID NO:397. In yet another specific embodiment, the organism is a yeast.

Another embodiment of the present invention is a unicellular organism for producing a diterpene or diterpene precursor, comprising an exogenous polynucleotide sequence encoding a polypeptide having an amino acid sequence of a geranylgeranyl pyrophosphate synthase under the control of a promoter operable in said organism; an isolated polynucleotide sequence encoding a polypeptide having an amino acid sequence of a diterpene synthase under the control of a promoter operable in said organism; an exogenous polynucleotide sequence encoding a polypeptide having an amino acid sequence of a soluble form of HMG-CoA reductase under control of a promoter operable in said organism; and an exogenous polynucleotide sequence encoding a polypeptide having an amino acid sequence of gene that confers to said organism an increase in sterol metabolic flux as compared to native sterol metabolic flux levels. In a specific embodiment, the amino acid sequence of the geranylgeranyl pyrophosphate synthase is SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84 or SEQ ID NO:85. In another specific embodiment, the amino acid sequence of said diterpene synthase is SEQ ID NO:383; SEQ ID NO:384; SEQ ID NO:385; SEQ ID NO:386; SEQ ID NO:387; SEQ ID NO:388; SEQ ID NO:389; SEQ ID NO:390; SEQ ID NO:391; SEQ ID NO:392; SEQ ID NO:393; SEQ ID NO:394; SEQ ID NO:395; SEQ ID NO:396 or SEQ ID NO:398. In a specific embodiment, the organism is a yeast.

In another embodiment of the present invention there is a method of producing a diterpene, comprising the steps of growing a culture of cells, wherein at least one cell in said culture is the unicellular organism containing exogenous geranylgeranyl pyrophosphate synthase and diterpene synthase nucleic acid sequences, under conditions wherein said diterpene is produced; and removing said diterpene from said culture. In a specific embodiment, the growing step occurs in the presence of a polyaromatic resin. In another specific embodiment, the removal step occurs through filtration or extraction. In another specific embodiment, the removal step occurs through filtration. In an additional specific embodiment, the polyaromatic resin is in a weight-to-volume ratio of at least about 5%. In an additional specific embodiment the unicellular organism is a yeast. In another specific embodiment the unicellular organism is a bacteria. In another specific embodiment of the present invention, the nucleic acid sequence of said geranylgeranyl pyrophosphate synthase is regulated by an inducible GAL1 promoter and wherein the growing step occurs in the presence of about 2% galactose. In another specific embodiment, the nucleic acid sequence encoding said geranylgeranyl pyrophosphate synthase and said nucleic acid sequence encoding said diterpene synthase are both regulated by an inducible GAL1 promoter and wherein said growing step occurs in about 2% galactose.

In another embodiment there is a method of producing a diterpene, comprising the steps of growing a culture of cells, wherein at least one cell in said culture is the unicellular organism having an exogenous nucleic acid sequence encoding a geranylgeranyl pyrophosphate synthase, an exogenous nucleic acid sequence encoding a soluble form of HMG-CoA reductase and an exogenous nucleic acid sequence encoding a diterpene synthase, under conditions wherein said diterpene is produced; and removing the diterpene from the culture of cells. In a specific embodiment, the growing step occurs in the presence of a polyaromatic resin. In an additional specific embodiment, the polyaromatic resin is in a weight-to-volume ratio of at least about 5%. In an additional specific embodiment the unicellular organism is a yeast. In another specific embodiment the unicellular organism is a bacteria In another specific embodiment of the present invention, the nucleic acid sequence of said geranylgeranyl pyrophosphate synthase is regulated by an inducible GAL1 promoter and wherein the growing step occurs in the presence of at least about 2% galactose. In another specific embodiment, the nucleic acid sequence encoding said geranylgeranyl pyrophosphate synthase, the nucleic acid sequence encoding said HMG-CoA reductase and the nucleic acid sequence encoding the diterpene synthase are regulated by an inducible GAL1 promoters and wherein said growing step occurs in at least about 2% galactose.

In another embodiment there is a method of producing a diterpene, comprising the steps of growing a culture of cells, wherein at least one cell in said culture is the unicellular organism having an exogenous nucleic acid sequence encoding a geranylgeranyl pyrophosphate synthase, an exogenous nucleic acid sequence encoding a soluble form of HMG-CoA reductase, an exogenous nucleic acid sequence encoding a diterpene synthase and an exogenous nucleic acid sequence that confers to the organism an increase in sterol metabolic flux as compared to native sterol metabolic flux levels, under conditions wherein said diterpene is produced; and removing the diterpene from the culture of cells. In a specific embodiment, the growing step occurs in the presence of a polyaromatic resin. In an additional specific embodiment, the polyaromatic resin is in a weight-to-volume ratio of at least about 5%. In an additional specific embodiment the unicellular organism is a yeast. In another specific embodiment the unicellular organism is a bacteria. In another specific embodiment of the present invention, the nucleic acid sequence of said geranylgeranyl pyrophosphate synthase is regulated by an inducible GAL1 promoter and wherein the growing step occurs in the presence of at least about 2% galactose. In another specific embodiment, the nucleic acid sequence encoding said geranylgeranyl pyrophosphate synthase, the nucleic acid sequence encoding said HMG-CoA reductase and the nucleic acid sequence encoding the diterpene synthase are regulated by an inducible GAL1 promoters and wherein said growing step occurs in at least about 2% galactose.

In another embodiment there is a method of producing a diterpene precursor, comprising the steps of growing a culture of cells, wherein at least one cell in said culture is the unicellular organism having an exogenous nucleic acid sequence encoding a geranylgeranyl pyrophosphate synthase, an exogenous nucleic acid sequence encoding a soluble form of a HMG-CoA reductase, and an exogenous nucleic acid sequence that confers to the cell an increase in sterol metabolic flux as compared to native sterol metabolic flux levels, under conditions wherein said diterpene is produced; and removing the diterpene from the culture of cells. In a specific embodiment, the nucleic acid sequence that confers to said cell an increase in sterol metabolic flux is the upc2-1 allele. In a specific embodiment, the growing step occurs in the presence of a polyaromatic resin. In an additional specific embodiment, the polyaromatic resin is in a weight-to-volume ratio of at least about 5%. In an additional specific embodiment the unicellular organism is a yeast or a bacteria. In another specific embodiment of the present invention, the nucleic acid sequence of said geranylgeranyl pyrophosphate synthase is regulated by an inducible GAL1 promoter and wherein the growing step occurs in the presence of at least about 2% galactose. In another specific embodiment, the nucleic acid sequence encoding said geranylgeranyl pyrophosphate synthase and the nucleic acid sequence encoding the soluble form of the HMG-CoA reductase are regulated by an inducible GAL1 promoters and wherein said growing step occurs in at least about 2% galactose.

In another embodiment there is a method of producing a diterpene precursor, comprising the steps of growing a culture of cells, wherein at least one cell in said culture is the unicellular organism having an exogenous nucleic acid sequence encoding a geranylgeranyl pyrophosphate synthase, an exogenous nucleic acid sequence encoding a soluble form of a HMG-CoA reductase, and an exogenous nucleic acid sequence that confers to the cell an increase in sterol metabolic flux as compared to native sterol metabolic flux levels, under conditions wherein said diterpene precursor is produced. In a specific embodiment, the nucleic acid sequence that confers to said cell an increase in sterol metabolic flux is the upc2-1 allele. In a specific embodiment, the growing step occurs in the presence of a polyaromatic resin. In an additional specific embodiment, the polyaromatic resin is in a weight-to-volume ratio of at least about 5%. In an additional specific embodiment the unicellular organism is a yeast. In another specific embodiment the unicellular organism is a bacteria. In another specific embodiment of the present invention, the nucleic acid sequence of said geranylgeranyl pyrophosphate synthase is regulated by an inducible GAL1 promoter and wherein the growing step occurs in the presence of at least about 2% galactose. In another specific embodiment, the nucleic acid sequence encoding said geranylgeranyl pyrophosphate synthase, the nucleic acid sequence encoding the soluble form of the HMG-CoA reductase and the nucleic acid sequence encoding the diterpene synthase are regulated by an inducible GAL1 promoters and wherein said growing step occurs in at least about 2% galactose.

A method of producing a diterpene or diterpene precursor, comprising the steps of growing a culture of cells, wherein at least one cell in said culture is the unicellular organism having an exogenous polynucleotide sequence encoding a polypeptide having an amino acid sequence of a geranylgeranyl pyrophosphate synthase under the control of a promoter operable in said organism; an exogenous polynucleotide sequence encoding a polypeptide having an amino acid sequence of a diterpene synthase under the control of a promoter operable in said organism; an exogenous polynucleotide sequence encoding a polypeptide having an amino acid sequence of a soluble form of HMG-CoA reductase under control of a promoter operable in said organism; and an exogenous polynucleotide sequence encoding a polypeptide having an amino acid sequence of a gene that confers to said organism an increase in sterol metabolic flux as compared to native sterol metabolic flux levels, under conditions wherein said diterpene or diterpene precursor is produced.

In another embodiment of the present invention there is a method of producing a diterpene, comprising the steps of growing a culture of cells, wherein the culture comprises at least one cell having an exogenous nucleic acid sequence encoding a geranylgeranyl pyrophosphate synthase under control of a promoter operable in the cell, an exogenous nucleic acid sequence encoding a diterpene synthase under control of a promoter operable in the cell, an exogenous nucleic acid sequence encoding a soluble form of HMG-CoA reductase under control of a promoter operable in the cell and a nucleic acid sequence encoding a gene that confers an increase in sterol metabolic flux in the cell as compared to native sterol metabolic flux levels, wherein a metabolic pathway in the cell comprises a process which converts farnesyl pyrophosphate to a triterpene or sterol, wherein the process is modified and under conditions wherein said diterpene is produced; and removing said diterpene from the culture. In a specific embodiment, the modification of the metabolic pathway occurs at an enzyme selected from the group consisting of squalene synthase, squalene epoxidase, lanosterol synthase, or a combination thereof. In another specific embodiment, the modification is the result of an alteration in a nucleic acid sequence which encodes the enzyme, an alteration in expression of a nucleic acid sequence which encodes the enzyme, an alteration in translation or proteolysis of the enzyme, or a combination thereof.

In another embodiment of the present invention there is a method of producing a diterpene precursor, comprising the steps of growing a culture of cells, wherein the culture comprises at least one cell comprising an exogenous nucleic acid sequence encoding a geranylgeranyl pyrophosphate synthase, an exogenous nucleic acid sequence encoding a soluble form of a HMG-CoA reductase, and an exogenous nucleic acid sequence encoding a gene that confers to the cell an increase in sterol metabolic flux as compared to native sterol metabolic flux levels, and wherein a metabolic pathway in the cell comprises a process which converts farnesyl pyrophosphate to a triterpene or sterol, wherein the process is modified and under conditions wherein said diterpene is produced; and removing said diterpene from the culture. In a specific embodiment, the modification of the metabolic pathway occurs at an enzyme selected from the group consisting of squalene synthase, squalene epoxidase, lanosterol synthase, or a combination thereof. In another specific embodiment, the modification is the result of an alteration in a nucleic acid sequence which encodes the enzyme, an alteration in expression of a nucleic acid sequence which encodes the enzyme, an alteration in translation or proteolysis of the enzyme, or a combination thereof.

In another embodiment of the present invention there is a method of producing a diterpene or a diterpene precursor, comprising the steps of growing a culture of cells, wherein the culture comprises at least one cell comprising an exogenous nucleic acid sequence encoding a polypeptide of an amino acid sequence of a geranylgeranyl pyrophosphate synthase, an exogenous nucleic acid sequence encoding a polypeptide of an amino acid sequence of a a diterpene synthase, an exogenous nucleic acid sequence encoding a polypeptide of an amino acid sequence of a soluble form of a HMG-CoA reductase and a upc2-1 amino acid sequence, wherein a metabolic pathway in the cell comprises a process which converts farnesyl pyrophosphate to a triterpene or sterol, wherein the process is modified and under conditions wherein said diterpene or diterpene precursor is produced. In a specific embodiment, the modification of the metabolic pathway occurs at an enzyme selected from the group consisting of squalene synthase, squalene epoxidase, lanosterol synthase, or a combination thereof. In another specific embodiment, the modification is the result of an alteration in a nucleic acid sequence which encodes the enzyme, an alteration in expression of a nucleic acid sequence which encodes the enzyme, an alteration in translation or proteolysis of the enzyme, or a combination thereof.

In another embodiment of the present invention there is a method of producing a diterpene, comprising the steps of growing a culture of cells, wherein the culture comprises at least one cell having an exogenous nucleic acid sequence encoding a geranylgeranyl pyrophosphate synthase under control of a promoter operable in the cell, an exogenous nucleic acid sequence encoding a diterpene synthase under control of a promoter operable in the cell, an exogenous nucleic acid sequence encoding a soluble form of HMG-CoA reductase under control of a promoter operable in the cell and an exogenous nucleic acid sequence encoding a gene that confers an increase in sterol metabolic flux in the cell as compared to native sterol metabolic flux levels, and wherein a prenyltransferase is modified, under conditions wherein the diterpene is produced. In a specific embodiment, the prenyltransferase is protein farnesyltransferase, protein geranylgeranyltransferase I alpha subunit, protein geranylgeranyltransferase I beta subunit, protein geranylgeranyltransferase II alpha subunit, protein geranylgeranyltransferase II beta subunit, or a combination thereof. In another specific embodiment, the modification is the result of an alteration in a nucleic acid sequence which encodes said enzyme, an alteration in expression of a nucleic acid sequence which encodes the enzyme, an alteration in translation or proteolysis of the enzyme, or a combination thereof.

In another embodiment of the present invention there is a method of producing a diterpene precursor, comprising the steps of growing a culture of cells, wherein the culture comprising an exogenous nucleic acid sequence encoding a geranylgeranyl pyrophosphate synthase, an exogenous nucleic acid sequence encoding a soluble form of a HMG-CoA reductase, and an exogenous nucleic acid sequence encoding a gene that confers to the cell an increase in sterol metabolic flux as compared to native sterol metabolic flux levels, and wherein a prenyltransferase is modified, under conditions wherein the diterpene precursor is produced. In an additional specific embodiment, the prenyltransferase is protein farnesyltransferase, protein geranylgeranyltransferase I alpha subunit, protein geranylgeranyltransferase I beta subunit, protein geranylgeranyltransferase II alpha subunit, protein geranylgeranyltransferase II beta subunit, or a combination thereof. In another specific embodiment, the modification is the result of an alteration in a nucleic acid sequence which encodes said enzyme, an alteration in expression of a nucleic acid sequence which encodes the enzyme, an alteration in translation or proteolysis of the enzyme, or a combination thereof.

In another embodiment of the present invention there is a method of producing a diterpene, comprising the steps of growing a culture of cells, wherein the cell comprises an exogenous nucleic acid sequence encoding a geranylgeranyl pyrophosphate synthase under control of a promoter operable in the cell, an exogenous nucleic acid sequence encoding a diterpene synthase under control of a promoter operable in the cell, an exogenous nucleic acid sequence encoding a soluble form of HMG-CoA reductase under control of a promoter operable in the cell and an exogenous nucleic acid sequence encoding a gene that confers an increase in sterol metabolic flux in the cell as compared to native sterol metabolic flux levels, and wherein a hexaprenylpyrophosphate synthetase is modified, under conditions wherein the geranylgeranyl pyrophosphate is produced. In another specific embodiment, the modification is the result of an alteration in a nucleic acid sequence which encodes said enzyme, an alteration in expression of a nucleic acid sequence which encodes the enzyme, an alteration in translation or proteolysis of the enzyme, or a combination thereof.

In another embodiment of the present invention there is a method of producing a diterpene precursor, comprising the steps of growing a culture of cells, wherein at least one cell comprises an exogenous nucleic acid sequence encoding a geranylgeranyl pyrophosphate synthase, an exogenous nucleic acid sequence encoding a soluble form of a HMG-CoA reductase, and an exogenous nucleic acid sequence encoding a gene that confers to the cell an increase in sterol metabolic flux as compared to native sterol metabolic flux levels, and wherein a hexaprenylpyrophosphate synthetase is modified, under conditions wherein the diterpene is produced. In another specific embodiment, the modification is the result of an alteration in a nucleic acid sequence which encodes said enzyme, an alteration in expression of a nucleic acid sequence which encodes the enzyme, an alteration in translation or proteolysis of the enzyme, or a combination thereof.

In another embodiment of the present invention there is a method of isolating a diterpene synthase, comprising the steps of growing a plurality of cells, wherein the cell comprises an exogenous nucleic acid sequence encoding a geranylgeranyl pyrophosphate synthase, an exogenous nucleic acid sequence encoding a soluble form of a HMG-CoA reductase, and an exogenous nucleic acid sequence encoding a gene that confers to the cell an increase in sterol metabolic flux as compared to native sterol metabolic flux levels, in the presence of a polyaromatic resin to make a cell/resin mixture, wherein at least one of said cells further comprises at least one isolated and purified nucleic acid sequence of a yeast expression library, wherein the expression of said nucleic acid sequence of the yeast expression library is regulated by an inducible promoter, under conditions wherein said expression is induced; filtering said cell/resin mixture; extracting said cell/resin mixture to produce an eluent; analyzing said eluent by a screening method, wherein said screening method is selected from the group consisting of chromatography, spectroscopy, or a combination thereof, and wherein said screening method identifies said nucleic acid sequence as encoding the diterpene synthase.

Other and further objects, features, and advantages would be apparent and eventually more readily understood by reading the following specification and be reference to the accompanying drawings forming a part thereof, or any examples of the presently preferred embodiments of the invention given for the purpose of the disclosure.

DETAILED DESCRIPTION OF THE INVENTION

Figure 1:
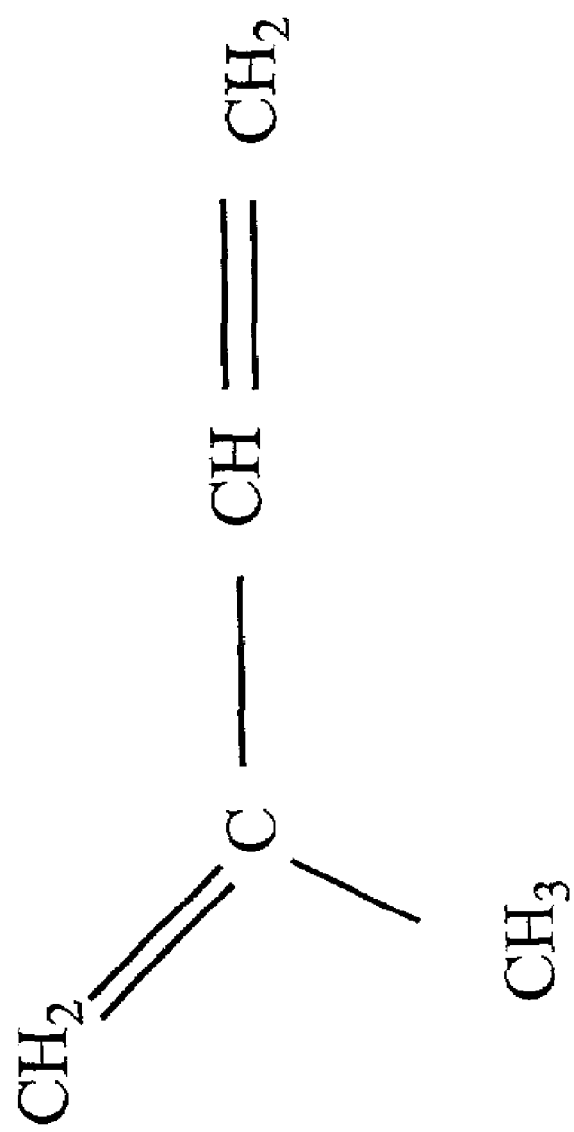
FIG. 1 illustrates a generic structure of isoprene.

It will be readily apparent to one skilled in the art that various embodiments and modifications may be made in the invention disclosed herein without departing from the scope and spirit of the invention.

As used in the specification, "a" or "an" may mean one or more. As used in the claim(s), when used in conjunction with the word "comprising", the words "a" or "an" may mean one or more than one. As used herein "another" may mean at least a second or more.

The technology of the present invention is related to the invention described in the U.S. Patent Application entitled, "*Ginkgo biloba* Levopimaradiene Synthase" filed on the same day and incorporated by reference herein.

I. Definitions

The term "diterpene" as used herein is defined as a terpene molecule having four isoprene units ($C_{20}$ compounds).

The term "diterpene precursor" as used herein is defined as a metabolite in a pathway that serves as a synthetic or biosynthetic precursor to the production of a diterpene. A preferred diterpene precursor is geranylgeranyl pyrophosphate but also includes farnesyl pyrophosphate and isopentenyl pyrophosphate.

The term "diterpene synthase" as used herein is defined as an enzyme that catalyzes biosynthesis of a diterpene. In a specific embodiment, the term "diterpene cyclase" is used herein to refer to a diterpene synthase that effects a cyclization reaction to produce a diterpene having at least one cyclic structure. A non-limiting example of a diterpene comprising three cyclic structures is abietadiene.

The term "downregulated" as used herein refers to the state of a metabolic pathway being altered in which a step or process in the pathway is decreased or downregulated, such as in activity of an enzyme or expression of a nucleic acid sequence, respectively. In a specific embodiment, the modification is the result of an alteration in a nucleic acid sequence which encodes an enzyme in the pathway, an alteration in expression of a nucleic acid sequence which encodes an enzyme in the pathway, or an alteration in translation or proteolysis of an enzyme in the pathway, or a combination thereof. A skilled artisan recognizes that there are commonly used standard methods in the art to obtain the alterations, such as by mutation.

The terms "exogenous nucleic acid sequence" and "exogenous polynucleotide" refer to a nucleic acid sequence or polynucleotide that has been prepared and provided to a cell. In one aspect, the nucleic acid sequence has been isolated and purified by methods well-known in the art and, optionally, modified. This nucleic acid sequence is then provided to a cell employing methods known in the art, thereby producing a recombinant cell. In another aspect, the terms refer to a non-native nucleic acid sequence that has been provided to a cell. For example, an allele that confers an increase in a flux of a metabolic pathway has been added to the cell of the present invention by conventional methods such as genetic cross, and, thus, represents an exogenous sequence as compared to the native cell.

The term "GGPP" as used herein is defined as geranylgeranyl pyrophosphate and employed interchangably in the art with geranlygeranyl diphosphate (e.g., "GGDP"). The acyclic carbon structure possesses four double bonds, which preferably at least one is in the E configuration.

Figure 6:
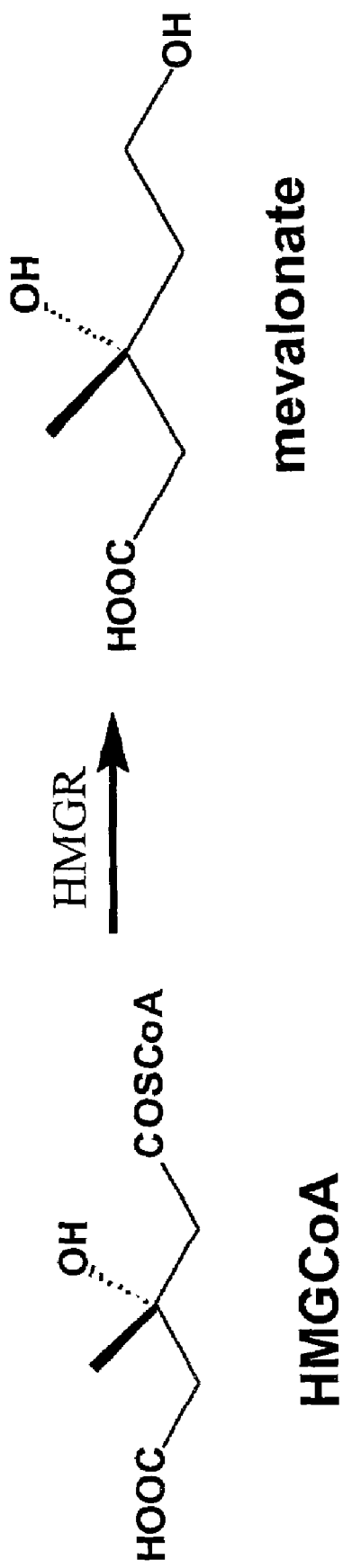
FIG. 6 illustrates the reaction catalyzed by HMG-CoA reductase (HMGR).
Figure 7:
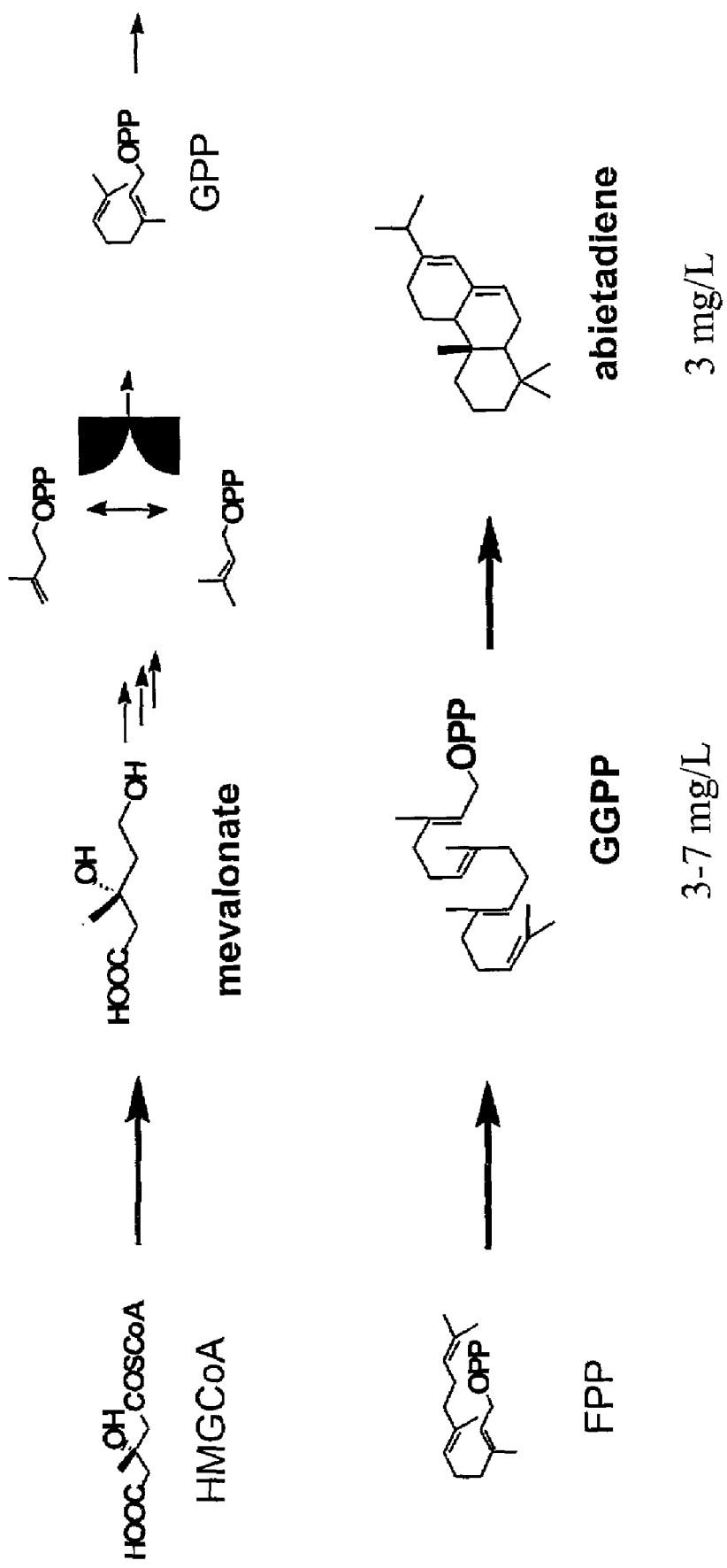
FIG. 7 demonstrates the increase in diterpene yield obtained with overexpression of a nucleic acid encoding HMG-CoA reductase.

The term "HMGR" as used herein is defined as HMG-CoA reductase. A skilled artisan is aware that HMGR catalyzes the reduction of 3-hydroxy-3-methylglutaryl Coenzyme A to mevalonate, which is interchangeably referred to as mevalonic acid (see FIG. 6).

The term "isoprene" as used herein is defined as a $C_5$ chemical unit as shown in FIG. 1.

The term "inducer" as used herein is defined as a compound, molecule or structure such as a promoter, that controls and effects a process. Specifically, one inducer of the present invention is galactose, which controls expression of a nucleic acid sequence of the present invention.

The terms "modified" or "modification" as used herein refer to the state of a metabolic pathway being altered in which a step or process in the pathway is decreased or downregulated or increased or upregulated, such as in activity of an enzyme or expression of a nucleic acid sequence. In a specific embodiment, the modification is the result of an alteration in a nucleic acid sequence which encodes an enzyme in the pathway, an alteration in expression of a nucleic acid sequence which encodes an enzyme in the pathway, or an alteration in translation or proteolysis of an enzyme in the pathway, or a combination thereof. Further, the modification is the result of introducing or exogenously providing to a cell having a metabolic pathway a nucleic acid sequence the effects a desired modification of the pathway. A skilled artisan recognizes that there are commonly used standard methods in the art to obtain the alterations, such as by mutation.

The term "monoterpene" as used herein is defined as a terpene having two isoprene units ($C_{10}$ compounds), wherein the monoterpene is a metabolite of geranyl diphosphate or geranyl pyrophosphate.

The term "sesquiterpene" as used herein is defined as a terpene having three isoprene units ($C_{15}$ compounds), wherein the sesquiterpene is a metabolite of farnesyl diphosphate or farnesyl pyrophosphate.

The term "soluble form" as used herein is defined as a form, such as an amino acid sequence, that demonstrates HMG-CoA reductase activity. In a specific embodiment, the soluble form contains no more than about three transmembrane domains.

The term "terpene" as used herein is defined a material comprising isopentene (also called isoprene) units. The structure of the isoprene unit comprising terpenes is shown in FIG. 1.

The term "triterpene" as used herein is defined as a terpene having six isoprene units ($C_{30}$ compounds), wherein the triterpene is a metabolite of squalene or oxidosqualene.

The term "under conditions wherein said diterpene is produced" as used herein is defined as an environment wherein a diterpene is produced, wherein such parameters as temperature, such as between about 28° C. and about 32° C., but preferably about 30° C., growth media content, which is well known in the art, availability of an inducer for an inducible promoter, and the like are provided to produce the diterpene.

The term "under conditions wherein said geranylgeranyl pyrophosphate is produced" and "under conditions wherein said GGPP is produced" as used herein is defined as an environment wherein geranylgeranyl pyrophosphate is produced. In specific embodiments, the conditions includes cultivation temperature, such as between about 28° C. and about 32° C., but preferably about 30° C. unless an alteration comprising a temperature-sensitive mutation has been employed, growth media content, which is well known in the art, availability of an inducer for an inducible promoter, and the like are provided to produce the geranylgeranyl pyrophosphate (GGPP).

The term "under conditions wherein said geranylgeraniol is produced" and "under conditions wherein said GGOH is produced" as used herein is defined as an environment wherein geranylgeraniol is produced. In specific embodiments, the conditions includes cultivation temperature, such as between about 28° C. and about 32° C., but preferably about 30° C. unless an alteration comprising a temperature-sensitive mutation has been employed, growth media content, which is well known in the art, availability of an inducer for an inducible promoter, and the like are provided to produce the geranylgeraniol (GGOH).

The term "unicellular organism" as used herein is defined as a non-human organism which is a single cell and is incapable of development into a multicellular organism. In a specific embodiment, this includes bacteria, such as *Escherichia coli*, and yeast, such as *Saccharomyces*. Preferably the unicellular organism comprises an isoprenoid biosynthetic pathway and/or a sterol biosynthetic pathway.

The term "upregulated" as used herein is defined as increased in expression of a particular nucleic acid sequence over native or wild type expression levels. The upregulation results from, for example, an increase in transcription of the sequence, an increase in stability of a messenger RNA of the sequence, a combination thereof, or through other means known in the art which increase levels of expression levels of a nucleic acid sequence. In a specific embodiment, the increase in expression is the result of a promoter operatively linked to the nucleic acid sequence which is not native to the nucleic acid sequence. In another specific embodiment, the increase in expression is the result of an inducible or constitutive promoter which regulates the nucleic acid sequence. In another specific embodiment, the increase in a cognate protein level of the nucleic acid sequence is the result of a promoter operatively linked to the amino acid sequence which is not native to the amino acid sequence.

II. The Present Invention

The present invention is directed to recombinant yeast, such as *Saccharomyces*, which is modified at at least one step in the sterol biosynthetic pathway to produce high levels of diterpene hydrocarbon(s) or a diterpene precursor such as GGPP. Yeast are readily genetically manipulated, and the metabolism of its major sterol, ergosterol, is well understood. Therefore, the yeast serve as a general production system, particularly because the yeast system is uniquely adaptable to further modify and biosynthesize other terpenes (including monoterpenes, sesquiterpenes, diterpenes and triterpenes) in vivo.

Another embodiment of the present invention is a recombinant bacteria, such as *E. coli*, which is modified at at least one step in the isoprenoid biosynthetic pathway to produce high levels of diterpene hydrocarbon(s) or a diterpene precursor such as GGPP. Bacteria are readily genetically manipulated and cultivated, and the isoprenoid metabolism of hopanoids, the prokaryotic cellular analog to sterols, is understood to comprise production in vivo of GGPP that is not a commecially feasible level.

Standard methods and reagents in the field of yeast molecular genetics, particularly regarding *Saccharomyces cerevisiae*, are well known in the art. References for such methods include *Methods in Yeast Genetics, 2000 Edition: A Cold Spring Harbor Laboratory Course Manual* (Burke et al., 2000) and *Current Protocols in Molecular Biology*, Chapter 13 (Ausubel et al., 1994), both incorporated by reference herein. A skilled artisan is aware that *Saccharomyces* is the yeast of choice, which includes many known species such as *S. cerevisiae, S. italicus, S. oviformis, S. capensis, S. chevalieri, S. douglasii, S. paradoxus, S. cariocanus, S. kudriavzevii, S. mikatae, S. bayanus* and *S. pastorianus*. In another embodiment, it is contemplated that filamentous fungi, such as *Aspergillus*, is used instead of a unicellular organism as defined herein. However, a skilled artisan recognizes that filamentous fingi, which normally develop into a multicellular septate organism, are unicellular in a pre-septate developmental stage.

In a preferred embodiment, the diterpene producing strain overexpresses a geranylgeranyl pyrophosphate synthase, overexpresses a diterpene synthase, overexpresses a soluble form of 3-hydroxy-3-methylglutaryl Co-A reductase, and contains a nucleic acid sequence that encodes a gene that confers an increase in sterol metabolic flux to the cell as compared to native sterol metabolic flux levels. That is, coexpression of a 3-hydroxy-3-methylglutaryl Co-A reductase or other enzymes that yield geranylgeranyl pyrophosphate allows production of geranylgeranyl pyrophosphate metabolites which include geranylgeraniol, diterpene hydrocarbon(s), further metabolites and related compounds. One non-limiting example of a nucleic acid sequence the encodes a gene that confers an increase in sterol metabolic flux is upc2-1. Genes that effect similar increases in sterol metabolic flux to the cell are contemplated as their effect is expected to increase the amount of diterpene produced in the recombinant cell. Incubation in the presence of a polyaromatic resin allows the product(s) to be adsorbed extracellularly, which greatly simplifies recovery and increases isolated yields. In specific embodiments, one or more additional enzymes are employed to further metabolize the diterpene synthase product (i.e., an oxidoreductase). In a preferred embodiment, the engineered unicellular organism is grown in the presence of at least about 5% (w/v) sterile polyaromatic resin-supplemented media.

A yeast cell of the present invention to produce a diterpene precursor preferably has at least one of the following: an exogenous polynucleotide encoding a polypeptide of amino acid sequence of a geranylgeranyl pyrophosphate synthase under the control of a promoter operable in the yeast, an exogenous nucleic acid sequence encoding a polypeptide of amino acid sequence of a HMG-CoA reductase under control of a promoter operable in the yeast, and/or an exogenous polynucleotide encoding a polypeptide that confers an increase in sterol metabolic flux to the cell as compared to native sterol metabolic flux levels. It is understood that a yeast cell that is desired to produce diterpenes in vivo must further comprise an exogenous polynucleotide encoding a polypeptide of amino acid sequence of a diterpene synthase under the control of a promoter operable in the yeast.

In specific embodiments, the yeast cell comprises a yeast geranylgeranyl pyrophosphate synthase, a diterpene synthase, a truncated form of HMG-CoA reductase, and a nucleic acid sequence encoding a gene that confers an increase in sterol metabolic flux. The geranylgeranyl pyrophosphate synthase originated in other organisms are also contemplated in specific embodiments. In one embodiment, a yeast cell is manipulated by standard molecular genetics methods to additionally contain BTS1, and/or the truncated HMG-CoA reductase, and/or the nucleic acid sequence that confers an increase in sterol metabolic flux. The nucleic acids are chromosome bound to minimize antibiotic selection requirements or are episomally borne and maintained in the cell by a selection or a functional means. Furthermore, the nucleic acid sequences of the present invention are preferably regulated by an inducible promoter, such as GAL1, CUP1 or MET3, to provide a means of external control of GGPP biosynthesis. In an alternative embodiment, a constitutive promoter such as the PGK promoter or the ADH promoter is utilized. In a specific embodiment, the constitutive promoter is employed to control expression of the diterpene synthase. In a preferred embodiment, the constitutive promoters are strong promoters.

In the specific embodiment wherein one or more nucleic acid sequences are included in the yeast cell to modify GGPP and/or utilize GGPP as a substrate for subsequent syntheses, this sequence(s) is contained on a multicopy plasmid bearing a selection means. In the specific embodiment wherein abietadiene is generated from the GGPP biosynthesis pathway, the abietadiene cyclase (e.g., diterpene synthase) is plasmid-borne within the cell and selected for by standard means.

In a specific embodiment, a normative nucleic acid sequence is incorporated into a yeast cell. Advantages of employing native nucleic acid and amino acid sequences includes, for example, cellular recognition of the recombinant structure. However, as a skilled artisan is aware, the cellular recognition has a disadvantage in that, for example, the recombinant structure is a highly regulated structure in the cell. Thus, accumulating the structure in vivo effects metabolic and regulatory mechanisms that are adverse to diterpene and diterpene precursor production.

A skilled artisan is aware that in the specific embodiments wherein there is variability in isolated and/or production yields, yet still highly improved over yields generated in the absence of a GGPP synthase, a soluble form of HMG-CoA reductase, and a nucleic acid encoding a gene that confers an increase in the sterol metabolic flux. This variability is due, for example, to the initiation of native regulatory mechanisms, the accumulation of hydrolyzed diterpene precursor, the transportation mechanisms responsible for molecular exportation, and/or other unknown mechanistic events controlling sterol biosynthesis.

In the specific embodiment wherein a plant nucleic acid sequence is utilized, a skilled artisan is aware that, for instance, such as is required by *E. coli*, a plastidyl targeting sequence is be identified and removed. If the targeting sequence does not occur, the structural products are vulnerable to incorporation into inclusion bodies. However, the significant surplus of precursor generated by the compositions and methods of the present invention allow use of the full length plant nucleic acid sequence, which is a significant advantage of the present invention. In particular, this is advantageous in the methods of the present invention wherein a diterpene synthase is identified by enzymatic activity in the compositions of the present invention.

Alternatively, a unicellular organism comprising an isolated polypeptide encoding an amino acid sequence of a GGPP synthase, the soluble form of HMG-CoA reductase, the diterpene synthase, a gene that confers an increase in sterol metabolic flux, the squalene synthase, the hexaprenylpyrophosphate synthetase and/or the prenyltransferase are within the scope of the present invention. Non-limiting examples of amino acid sequences are provided herein.

In other embodiments, a modification is made that decreases, downregulates, diminishes or removes biosynthetic pathways that compete for GGPP bioavailability. In another specific embodiment, a hexaprenylpyrophosphate synthetase is modified to increase FPP flux into the engineered GGPP biosynthesis pathway. An example of a hexaprenylpyrophosphate synthetase is COQ1 (GenBank Accession No. J05547; SEQ ID NO:401). Hexaprenylpyrophosphate is the committed step of pathways which produce dolichols and ubiquinones. In an additional specific embodiment, a prenyltransferase is modified. Prenyltransferases are well known in the art. In a specific embodiment, the site of inhibition is protein farnesyltransferase (such as STE14; GenBank Accession No. L15442 (SEQ ID NO:402) or GenBank Accession No. L07952 (SEQ ID NO:403)), protein geranylgeranyltransferase I alpha subunit (such as CDC43; GenBank Accession No. M31114; SEQ ID NO:404), protein geranylgeranyltransferase I beta subunit (such as RAM2; GenBank Accession No. M88584; SEQ ID NO:405), protein geranylgeranyltransferase II alpha subunit (such as BET2; GenBank Accession No. M26597; SEQ ID NO:406), protein geranylgeranyltransferase II beta subunit (such as BET4; GenBank Accession No. U14132; SEQ ID NO:407), or a combination thereof.

A skilled artisan is aware of sequence repositories, such as GenBank, to obtain nucleic acid and amino acid sequences utilized in the present invention. Examples of geranylgeranyl pyrophosphate synthase nucleic acid sequences for the present invention include the following: U31632 (SEQ ID NO:1); AF049658 (SEQ ID NO:2); AK025139 (SEQ ID NO:3); AB000835 (SEQ ID NO:4); AJ276129 (SEQ ID NO:5); AB034250 (SEQ ID NO:6); AB034249 (SEQ ID NO:7); AW132388 (SEQ ID NO:8); AW034766 (SEQ ID NO:9); AI496168 (SEQ ID NO:10); AF081514 (SEQ ID NO:11); AF020041 (SEQ ID NO:12); X98795 (SEQ ID NO:13); X92893 (SEQ ID NO:14); X80267 (SEQ ID NO:15); L37405 (SEQ ID NO:16); U15778 (SEQ ID NO:17); L40577 (SEQ ID NO:18); M87280 (SEQ ID NO:19); L25813 (SEQ ID NO:20); and AF049659 (SEQ ID NO:21). A skilled artisan is aware that sequences unrelated to geranylgeranyl pyrophosphate synthase in those sequences which comprise large regions of the genome of a particular organism are not within the scope of the invention. In a preferred embodiment, SEQ ID NO:1 is utilized as a geranylgeranyl pyrophosphate synthase nucleic acid sequence in the cell of the invention.

Examples of geranylgeranyl pyrophosphate synthase amino acid sequences for the present invention include the following: AAA83262.1 (SEQ ID NO:22); AAC05595.1 (SEQ ID NO:23); AAC05273.1 (SEQ ID NO:24); NP_043281.1 (SEQ ID NO:25); BAB18334.1 (SEQ ID NO:26); AAC68232.1 (SEQ ID NO:27); CAC12434.1 (SEQ ID NO:28); BAB02385.1 (SEQ ID NO:29); CAB94793.1 (SEQ ID NO:30); AAF38891.1 (SEQ ID NO:31); BAA23157.1 (SEQ ID NO:32); BAA19583.1 (SEQ ID NO:33); CAB89115.1 (SEQ ID NO:34); AAD12206.1 (SEQ ID NO:35); AAD08933.1 (SEQ ID NO:36); CAB80510 (SEQ ID NO:37); CAB80347.1 (SEQ ID NO:38); CAB38744.1 (SEQ ID NO:39); BAA16690.1 (SEQ ID NO:40); AAD38295.1 (SEQ ID NO:41); BAA86285.1 (SEQ ID NO:42); BAA86284.1 (SEQ ID NO:43); CAB53152.1 (SEQ ID NO:44); CAB56064.1 (SEQ ID NO:45); BAA77251 (SEQ ID NO:46); CAB16803.1 (SEQ ID NO:47); CAB37502.1 (SEQ ID NO:48); AAD16018.1 (SEQ ID NO:49); AAC77874.1 (SEQ ID NO:50); CAA17477.1 (SEQ ID NO:51); AAC06913.1 (SEQ ID NO:52); CAA67330.1 (SEQ ID NO:53); AAB67731.1 (SEQ ID NO:54); CAA63486.1 (SEQ ID NO:55); CAA56554.1 (SEQ ID NO:56); AAA96328.1 (SEQ ID NO:57); AAA91949.1 (SEQ ID NO:58); AAA86688.1 (SEQ ID NO:59); AAA81879.1 (SEQ ID NO:60); AAA81312.1 (SEQ ID NO:61); AAA32797.1 (SEQ ID NO:62); BAB01876 (SEQ ID NO:63); BAA23157 (SEQ ID NO:64); AAD43148 (SEQ ID NO:65); NP_043281 (SEQ ID NO:66); BAB18334 (SEQ ID NO:67); E81650 (SEQ ID NO:68); T36967 (SEQ ID NO:69); S76966 (SEQ ID NO:70); A72041 (SEQ ID NO:71); T02429 (SEQ ID NO:72); S74538 (SEQ ID NO:73); S71230 (SEQ ID NO:74); S71231 (SEQ ID NO:75); AAC05595 (SEQ ID NO:76); AAC05273 (SEQ ID NO:77); BAB02387 (SEQ ID NO:78); BAB01936 (SEQ ID NO:79); AAF39709 (SEQ ID NO:80); BAA23158 (SEQ ID NO:81); E70365 (SEQ ID NO:82); S49625 (SEQ ID NO:83); P34802 (SEQ ID NO:84); and P80042 (SEQ ID NO:85). In a preferred embodiment, SEQ ID NO:22 is utilized as a geranylgeranyl pyrophosphate synthase amino acid sequence in the cell.

One non-limiting example of a gene that confers an increase to sterol metabolic flux as compared to native sterol metabolic flux levels is the upc2-1 allele. The upc2-1 allele comprises a guanine to adenine transition in the open reading frame designated YDR213W on chromosome IV (Leak et al., 1999; incorporated by reference herein in its entirety). The nucleic acid sequence is known and/or obtained through GenBank Accession No. Z68194 (SEQ ID NO:399), and Leak et al. (1999) describe the mutations associated with the upc2-1 allele. Incorporation of the upc2-1 allele conferred an increase in sterol metabolic flux as compared to native sterol metabolic flux levels, and thus, demonstrates that other such genes that confer the same biological activity, e.g., increase sterol metabolic flux levels, are expected to increase production in vivo of a diterpene and a diterpene precursor.

In a preferred embodiment of the present invention, a soluble form of HMG-CoA reductase is utilized. A skilled artisan is aware that this requires removal of hydrophobic sequences responsible for conferring insolubility to the gene product, such as transmembrane domains, and is furthermore aware of standard methods to achieve such removal from the sequence. Examples of HMG-CoA reductase nucleic acid sequences, which in specific embodiments may be altered to achieve solubility of the reductase for the present invention, include the *Saccharomyces cerevisiae* open reading frame found on chromosome XIII at locus YML075C (SEQ ID NO:86); NM_000859 (SEQ ID NO:87); X00494 (SEQ ID NO:88); AF273765 (SEQ ID NO:89); AF273764 (SEQ ID NO:90); AF273763 (SEQ ID NO:91); AF273762 (SEQ ID NO:92); AF273761 (SEQ ID NO:93); AF273760 (SEQ ID NO:94); AF273759 (SEQ ID NO:95); AF273758 (SEQ ID NO:96); AF273757 (SEQ ID NO:97); AF273756 (SEQ ID NO:98); AF273755 (SEQ ID NO:99); AF273754 (SEQ ID NO:100); AF290098 (SEQ ID NO:101); AF290096 (SEQ ID NO:102); AF290090 (SEQ ID NO:103); AF290088 (SEQ ID NO:104); AF290086 (SEQ ID NO:105); AF071750 (SEQ ID NO:106); AB037907 (SEQ ID NO:107); AF155593 (SEQ ID NO:108); X58370 (SEQ ID NO:109); AF162705 (SEQ ID NO:110); AF159136 (SEQ ID NO:111); AF159138 (SEQ ID NO:112); AB015627 (SEQ ID NO:113); AB015626 (SEQ ID NO:114); AV374599 (SEQ ID NO:115); AV317420 (SEQ ID NO:116); AV317328 (SEQ ID NO:117); AV317132 (SEQ ID NO:118); AV277976 (SEQ ID NO:119); AV259312 (SEQ ID NO:120); AV237573 (SEQ ID NO:121); AF142473 (SEQ ID NO:122); E17178 (SEQ ID NO:123); E17177 (SEQ ID NO:124); AF110382 (SEQ ID NO:125); AB021862 (SEQ ID NO:126); U97683 (SEQ ID NO:127); AI326595 (SEQ ID NO:128); U33178 (SEQ ID NO:129); U30179 (SEQ ID NO:130); L34829 (SEQ ID NO:131); L34824 (SEQ ID NO:132); AB012603 (SEQ ID NO:133); AA982887 (SEQ ID NO:134); AF038045 (SEQ ID NO:135); AA710790 (SEQ ID NO:136); AA597171 (SEQ ID NO:137); AA517939 (SEQ ID NO:138); U51986 (SEQ ID NO:139); U51985 (SEQ ID NO:140); AA260731 (SEQ ID NO:141); AA109510 (SEQ ID NO:142); L76979 (SEQ ID NO:143); X70034 (SEQ ID NO:144); X94308 (SEQ ID NO:145); X68651 (SEQ ID NO:146); X94307 (SEQ ID NO:147); A10474 (SEQ ID NO:148); A10471 (SEQ ID NO:149); A10468 (SEQ ID NO:150); A10465 (SEQ ID NO:151); A10462 (SEQ ID NO:152); X55286 (SEQ ID NO:153); J04537 (SEQ ID NO:154); A10473 (SEQ ID NO:155); A10470 (SEQ ID NO:156); A10467 (SEQ ID NO:157); M15959 (SEQ ID NO:158); M62633 (SEQ ID NO:159); M62766 (SEQ ID NO:160); M12705 (SEQ ID NO:161); M22002 (SEQ ID NO:162); L19261 (SEQ ID NO:163); J04200 (SEQ ID NO:164); J03523 (SEQ ID NO:165); M27294 (SEQ ID NO:166); M24015 (SEQ ID NO:167); or a combination thereof.

Examples of HMG-CoA reductase amino acid sequences that are subsequently altered to achieve solubility of the reductase for the present invention include the following: NP_013636.1 (SEQ ID NO:168); NP_000850.1 (SEQ ID NO:169); CAA25189.1 (SEQ ID NO:170); AAG02454.1 (SEQ ID NO:171); AAG02449.1 (SEQ ID NO:172); AAG02434.1 (SEQ ID NO:173); AAG02429 (SEQ ID NO:174); AAG02423.1 (SEQ ID NO:175); AAD20975.2 (SEQ ID NO:176); BAB07821.1 (SEQ ID NO:177); AAD38406.1 (SEQ ID NO:178); CAA41261.1 (SEQ ID NO:179); AAF80475.1 (SEQ ID NO:180); AAF80374.1 (SEQ ID NO:181); BAA74566.1 (SEQ ID NO:182); BAA74565 (SEQ ID NO:183); AAD47596.1 (SEQ ID NO:184); AAD38873.1 (SEQ ID NO:185); BAA36291.1 (SEQ ID NO:186); AAD09278 (SEQ ID NO:187); AAC46885.1 (SEQ ID NO:188); AAC37437.1 (SEQ ID NO:189); AAC37436.1 (SEQ ID NO:190); AAC37435.1 (SEQ ID NO:191); AAC37434.1 (SEQ ID NO:192); AAC37433.1 (SEQ ID NO:193); AAC37432.1 (SEQ ID NO:194); AAC37431.1 (SEQ ID NO:195); BAA31937.1 (SEQ ID NO:196); AAC05089.1 (SEQ ID NO:197); AAC05088.1 (SEQ ID NO:198); AAB67527.1 (SEQ ID NO:199); BAA06492.1 (SEQ ID NO:200); AAB52552.1 (SEQ ID NO:201); AAB52551.1 (SEQ ID NO:202); AAB39277.1 (SEQ ID NO:203); CAA49628.1 (SEQ ID NO:204); CAA63971.1 (SEQ ID NO:205); CAA48610.1 (SEQ ID NO:206); CAA63970.1 (SEQ ID NO:207); CAA39001.1 (SEQ ID NO:208); AAA76821.1 (SEQ ID NO:209); CAA00908.1 (SEQ ID NO:210); CAA00907.1 (SEQ ID NO:211); CAA00906.1 (SEQ ID NO:212); CAA00905.1 (SEQ ID NO:213); CAA00904.1 (SEQ ID NO:214); AAA67317.1 (SEQ ID NO:215); AAA37819.1 (SEQ ID NO:216); AAA37077.1 (SEQ ID NO:217); AAA34677.1 (SEQ ID NO:218); AAA32814.1 (SEQ ID NO:219); AAA30060.1 (SEQ ID NO:220); AAA29896.1 (SEQ ID NO:221); AAA25894.1 (SEQ ID NO:222); AAA25837.1 (SEQ ID NO:223); P43256 (SEQ ID NO:224); A23586 (SEQ ID NO:225); S12554 (SEQ ID NO:226); S72194 (SEQ ID NO:227); T07112 (SEQ ID NO:228); S56715 (SEQ ID NO:229); S56714 (SEQ ID NO:230); S56712 (SEQ ID NO:231); S56711 (SEQ ID NO:232); S56710 (SEQ ID NO:233); S33175 (SEQ ID NO:234); 028538 (SEQ ID NO:235); AAA25837 (SEQ ID NO:236); O26662 (SEQ ID NO:237); Q58116 (SEQ ID NO:238); Q59468 (SEQ ID NO:239); P54960 (SEQ ID NO:240); P48019 (SEQ ID NO:241); P48020 (SEQ ID NO:242); Q01559 (SEQ ID NO:243); Q03163 (SEQ ID NO:244); Q00583 (SEQ ID NO:245); P13702 (SEQ ID NO:246); P14891 (SEQ ID NO:247); Q9YAS4 (SEQ ID NO:248); Q9Y7D2 (SEQ ID NO:249); Q9XHL5 (SEQ ID NO:250); Q9XEL8 (SEQ ID NO:251); Q9V1R3 (SEQ ID NO:252); Q9V1R3 (SEQ ID NO:253); Q41437 (SEQ ID NO:254); O76819 (SEQ ID NO:255); O74164 (SEQ ID NO:256); O64967 (SEQ ID NO:257); O64966 (SEQ ID NO:258); O59469 (SEQ ID NO:259); O51628 (SEQ ID NO:260); O24594 (SEQ ID NO:261); NP_000850 (SEQ ID NO:262); CAA25189 (SEQ ID NO:263); NP_013555 (SEQ ID NO:264); NP_013308 (SEQ ID NO:265); AAA36989 (SEQ ID NO:266); Q12649 (SEQ ID NO:267); P04035 (SEQ ID NO:268); AAG21343 (SEQ ID NO:269); AAG02454 (SEQ ID NO:270); AAG02449 (SEQ ID NO:271); AAG02434 (SEQ ID NO:272); AAG02429 (SEQ ID NO:273); AAG02423 (SEQ ID NO:274); AAD20975 (SEQ ID NO:275); BAB07821 (SEQ ID NO:276); AAD38406 (SEQ ID NO:277); AAF80475 (SEQ ID NO:278); AAF80374 (SEQ ID NO:279); AAF80373 (SEQ ID NO:280); Q12577 (SEQ ID NO:281); BAA74566 (SEQ ID NO:282); BAA74565 (SEQ ID NO:283); P54869 (SEQ ID NO:284); O02734 (SEQ ID NO:285); O08424 (SEQ ID NO:286); Q10283 (SEQ ID NO:287); Q29512 (SEQ ID NO:288); P51639 (SEQ ID NO:289); P54839 (SEQ ID NO:290); P54874 (SEQ ID NO:291); Q01581 (SEQ ID NO:292); P54872 (SEQ ID NO:293); P54871 (SEQ ID NO:294); P54873 (SEQ ID NO:295); P54868 (SEQ ID NO:296); P54870 (SEQ ID NO:297); P54961 (SEQ ID NO:298); P48021 (SEQ ID NO:299); P48022 (SEQ ID NO:300); P34136 (SEQ ID NO:301); P34135 (SEQ ID NO:302); Q01237 (SEQ ID NO:303); P20715 (SEQ ID NO:304); P16237 (SEQ ID NO:305); P09610 (SEQ ID NO:306); P14773 (SEQ ID NO:307); P00347 (SEQ ID NO:308); P12684 (SEQ ID NO:309); P29058 (SEQ ID NO:310); P12683 (SEQ ID NO:311); P29057 (SEQ ID NO:312); P17425 (SEQ ID NO:313); P13704 (SEQ ID NO:314); P23228 (SEQ ID NO:315); P22791 (SEQ ID NO:316); AAD47596 (SEQ ID NO.317); 5542336 (SEQ ID NO:318); 5542335 (SEQ ID NO:319); 5542334 (SEQ ID NO:320); 5542333 (SEQ ID NO:321); AAD38873 (SEQ ID NO:322); BAA36291 (SEQ ID NO:323); AAD09278 (SEQ ID NO:324); AAC46885 (SEQ ID NO:325); AAC37437 (SEQ ID NO:326); AAC37435 (SEQ ID NO:327); AAC37434 (SEQ ID NO:328); AAC37433 (SEQ ID NO:329); AAC37432 (SEQ ID NO:330); AAC37431 (SEQ ID NO:331); AAC37436 (SEQ ID NO:332); BAA31937 (SEQ ID NO:333); AAC05089 (SEQ ID NO:334); AAC05088 (SEQ ID NO:335); AAB67527 (SEQ ID NO:336); AAB52552 (SEQ ID NO:337); AAB52551 (SEQ ID NO:338); AAB39277 (SEQ ID NO:339); CAA49628 (SEQ ID NO:340); 2116416F (SEQ ID NO:341); 2116416E (SEQ ID NO:342); 2116416D (SEQ ID NO:343); 2116416C (SEQ ID NO:344); 2116416B (SEQ ID NO:345); 2116416A (SEQ ID NO:346); CAA63971 (SEQ ID NO:347); CAA63970 (SEQ ID NO:348); CAA39001 (SEQ ID NO:349); CAA00906 (SEQ ID NO:350); CAA00907 (SEQ ID NO:351); CAA00908 (SEQ ID NO:352); CAA00904 (SEQ ID NO:353); AAA67317 (SEQ ID NO:354); AAA37819 (SEQ ID NO:355); AAA37077 (SEQ ID NO:356); AAA32814 (SEQ ID NO:357); AAA29896 (SEQ ID NO:358); RDHYE (SEQ ID NO:359); and AAA25894 (SEQ ID NO:360).

Diterpene synthase nucleic acid sequences that are useful in the present invention include *Stevia rebaudiana* kaurene synthase (KS22-1) (GenBank Accession number AF097311; SEQ ID NO:361); *Stevia rebaudiana* kaurene synthase (KS1-1) (GenBank Accession number AF097310; SEQ ID NO:362); *Stevia rebaudiana* copalyl pyrophosphate synthase (Cpps1) (GenBank Accession No. AF034545; SEQ ID NO:412); *Taxus brevifolia* taxadiene synthase (TDC1) (GenBank Accession No. U48796; SEQ ID NO:363); *Phaeosphaeria* sp. L487 mRNA for ent-kaurene synthase (GenBank Accession No. AB003395; SEQ ID NO:364); *Abies grandis* abietadiene synthase (ac22) (GenBank Accession No. U50768; SEQ ID NO:365) (Stoffer-Vogel et al., 1996); *Ricinus communis* casbene synthase (GenBank Accession No. L32134; SEQ ID NO:366) (Hill et al., 1996); *Cucumis sativus* KS mRNA for ent-kaurene synthase (GenBank Accession No. AB045310; SEQ ID NO:367); *Lactuca sativa* LsKS1 mRNA for ent-kaurene synthase No 1 (GenBank Accession No. AB031205; SEQ ID NO:368); *Glycine max* sequence GenBank Accession No. BE473763 (SEQ ID NO:369); *Glycine max* sequence GenBank Accession No. AW759166 (SEQ ID NO:370); *Gibberella fujikuroi* mRNA for GfCPS/KS (GenBank Accession No. AB013295; SEQ ID NO:371); *Lotus japonicus* cDNA (GenBank Accession No. AI967851; SEQ ID NO:372); *Glycine max* sequence (GenBank Accession No. AI940878; SEQ ID NO:373); *Homo sapiens* sequence (GenBank Accession No. AI809939; SEQ ID NO:374); *Zea mays* kaurene synthase (KS) mRNA (GenBank Accession No. AF105149; SEQ ID NO:375); *Arabidopsis thaliana* chromosome 1 BAC T8K14 sequence (GenBank Accession No. AC007202; SEQ ID NO:376); *Arabidopsis thaliana* ent-kaurene synthase (GA2) mRNA (GenBank Accession No. AF034774; SEQ ID NO:377) (Sun and Kamiya, 1994); unknown source cDNA encoding ent-kaurene synthase A (GenBank Accession No. E12936; SEQ ID NO:378); *Mycobacterium tuberculosis* sequence (GenBank Accession No. AL009198; SEQ ID NO:379); *Pisum sativum* ent-kaurene synthase A (LS) mRNA (GenBank Accession No. U63652; SEQ ID NO:380); *Cucurbita maxima* ent-kaurene synthase B mRNA (GenBank Accession No. U43904; SEQ ID NO:381) (Yamaguchi et al., 1996); and *Zea mays* kaurene synthase A (An1) mRNA (GenBank Accession No. L37750; SEQ ID NO:382) (Bensen et al., 1995).

Corresponding diterpene synthase amino acid sequences include *Stevia rebaudiana* kaurene synthase (KS22-1) (GenBank Accession number AAD34295.1 (SEQ ID NO:383); *Stevia rebaudiana* kaurene synthase (KS1-1) (GenBank Accession number AAD34294.1; SEQ ID NO:384); *Stevia rebaudiana* copalyl pyrophosphate synthase (Cpps1) (GenBank Accession No. AAB87091.1; SEQ ID NO:385); *Taxus brevifolia* taxadiene synthase (TDC1) (GenBank Accession No. AAC49310.1; SEQ ID NO:386); *Phaeosphaeria* sp. L487 mRNA for ent-kaurene synthase (GenBank Accession No. BAA22426.1; SEQ ID NO:387); *Abies grandis* abietadiene synthase (ac22) (GenBank Accession No. AAB05407.1; SEQ ID NO:388); *Cucumis sativus* KS mRNA for ent-kaurene synthase (GenBank Accession No. BAB19275.1; SEQ ID NO:389); *Lactuca sativa* LsKS1 mRNA for ent-kaurene synthase No 1 (GenBank Accession No. BAB12441.1; SEQ ID NO:390); *Gibberella fujikuroi* mRNA for GfCPS/KS (GenBank Accession No. BAA84917.1; SEQ ID NO:391); *Zea mays* kaurene synthase (KS) mRNA (GenBank Accession No. AAD34319.1; SEQ ID NO:392); *Mycobacterium tuberculosis* sequence (GenBank Accession No. CAA15731.1; SEQ ID NO:393); *Pisum sativum* ent-kaurene synthase A (LS) mRNA (GenBank Accession No. AAB58822.1; SEQ ID NO:394); *Cucurbita maxima* ent-kaurene synthase B mRNA (GenBank Accession No. AAB39482.1; SEQ ID NO:395); *Zea mays* kaurene synthase A (An1) mRNA (GenBank Accession No. AAA73960.1; SEQ ID NO:396).

In a specific embodiment, a *Ginkgo biloba* levopimaradiene synthase nucleic acid sequence (SEQ ID NO:397), which encodes the amino acid sequence of SEQ ID NO:398, is utilized for a diterpene synthase in the present invention, wherein the sequences are the subject of a U.S. patent application filed on the same day as this present application and is entitled, "*Ginkgo biloba* Levopimaradiene Synthase," incorporated by reference herein.

III. Terpenes

Terpenes are well known in the art, including geraniol or limonene (monoterpenes), farnesol or γ-bisabolene (sesquiterpenes), and squalene or β-amyrin (a triterpene). They are naturally-occurring compounds and are the most abundant components of essential oils of many plants and flowers. Terpenes are extracted from plants and flowers for a variety of purposes by distilling the plants with water. In a specific embodiment, terpenes are biosynthesized from acetyl-CoA (e.g., a derivitized acetate) and isopentenyl pyrophosphate. In one specific embodiment, terpenes are open chain systems or acyclic, such as geraniol, farnesol, geranylgeraniol and citronellal. Other terpenes are monocyclic, such as menthol and zingiberene, although the majority of terpenes are cyclic, such as β-santalol, β-cadinene, matricarin, and copaene. Carotenoids such as β-carotene, a precursor for vitamin A, and lycopene are also terpenes.

A major class of terpenes includes the sterols. A skilled artisan is aware of many reviews in the field of yeast sterol biosynthesis, such as Parks et al. (1995), Parks and Casey (1995), Paultauf and Kohlwein (1992), and Goldstein and Brown (1990), all of which are incorporated by reference herein in their entirety. The catalytic processes leading to the formation of FPP are commonly referred to as the isoprenoid pathway. The name originates from the isoprene unit ($C_5$), which subsequent to activation with a pyrophosphate, functions as the building blocks of terpenes. Easily detected by the integral number of $C_5$ units in their hydrocarbon skeleton, terpenes (i.e., isoprenoids) contribute to critical physiological roles in the cell, including tRNA modification, ubiquinone and dolichol biosynthesis, protein prenylation, and heme A biosynthesis.

IV. The upc2-1 Allele

In one aspect of the present invention, a mechanism that effects sterol metabolic flux is controlled. A nucleic acid sequence that encodes a gene that confers an increase on sterol metabolic flux was provided to a cell of a unicellular organism, and the amount of diterpene and diterpene alcohol was measured to determine the increase in sterol metabolic flux as compared to native sterol metabolic flux levels. The increase observed demonstrated that incorporating such nucleic acid sequences for expression in a resulting recombinant cell improves and enhances diterpene levels produced in vivo.

The representative example employed herein was a sterol uptake control mutant (upc⁻) that was isolated via ethylmethanesulfonate mutagenesis from wild-type *Saccharomyces cerevisiae* (Lewis et al., 1998). The sterol uptake control UPC2 allele upc2-1 (SEQ ID NO:399) increases the metabolic flux of sterol biosynthesis. It was originally cloned by calcium sensitivity, and the protein contains a DNA binding motif. The upc2-1 allele confers Erg⁻ Hem⁺ prototrophy and is a semi-dominant mutation. The mutation is a point mutation that results in an Asp residue instead of a Gly residue at amino acid 888. The upc2-1 allele (Crowley et al., 1998; Leak et al., 1999; both incorporated by reference in their entirety herein) is utilized in the compositions and methods of the present invention for both overcoming control of sterol importation uptake and increasing sterol biosynthesis (increasing metabolic flux). Another example of a gene that confers such activity is SUT 1 (SEQ ID NO:413; Karst et al., 2001). In another specific embodiment, two separate alleles which confer both phenotypes, or a different single allele which confers both phenotypes, are utilized in lieu of the upc2-1 allele.

V. HMG-CoA Reductase

Yeast have two isozymes of HMG-CoA reductase, Hmg1p and Hmg2p, produced from genes on separate chromosomes (Basson et al., 1986), although the vast majority of reductase activity under normal conditions is the result of Hmg1p activity. Null mutations in both genes cause lethality, yet null mutations in either gene alone are viable although survival is reduced (Basson et al., 1987). In a specific embodiment of the present invention, endogenous copies of both HMG1 and HMG2 remain intact in the cell which harbors the recombinant nucleic acid sequence encoding the soluble form of HMG-CoA reductase.

The cells of the present invention preferably comprise HMG-CoA reductase to improve production of diterpenes and diterpene precursors. HMG-CoA reductase is a rate-limiting enzyme in early sterol biosynthesis in eukaryotic cells. A skilled artisan is aware that increasing significant levels of HMG-CoA reductase in a yeast cell, which is membrane-bound in most organisms, results in generation of extensive membrane structures (Profant et al., 1999) that is detrimental to diterpene and diterpene precursor biosyntheses. Therefore, it is preferred that the form of HMG-CoA reductase utilized in the compositions of the present invention lack sequences responsible or associated with transmembrane domains. These structures are easily identified by standard means in the art, such as commercially available computer programs including Genetics Computer Group® (Madison, Wis.). To eliminate the rate limitation associated with this enzyme in the yeast *Saccharomyces cerevisiae*, a truncated HMG1 gene producing a form of the enzyme that lacks the membrane-binding region (i.e. amino acids 1–552; SEQ ID NO:400) (Polakowski et al., 1998) was utilized in the preferred embodiments.

A skilled artisan is aware that there are structurally distinct HMG-CoA reductases depending on the organism. For example, *Arabidopsis* HMG-CoA reductase lacks the membrane-spanning architecture present in other organisms, yet overexpression of the *Arabidopsis* nucleic acid sequence encoding HMG-CoA reductase in a yeast mutant suppresses its growth defect, suggesting the sequence is functionally interchangeable between the two organisms (Learned and Fink, 1989; incorporated by reference herein in its entirety). A similar experiment demonstrated restoration of normal growth to a CHO cell line which was HMG-CoA reductase-deficient (Goldstein and Brown, 1990). Thus, a skilled artisan is aware by the methods and design of Learned and Fink (1989) and by methods well known in the art how to test other HMG-CoA reductase sequences for functional complementation of a yeast HMG-CoA reductase defect. A skilled artisan is also aware that although structural differences exist between different organisms, the preferred aspects of the sequence are intracellular solubility and reductase activity. Therefore, in specific embodiments of the present invention, the nucleic acid sequence encoding a HMG-CoA reductase contains a deletion corresponding to an N-terminal sequence.

It is well known that there are two native *S. cerevisiae* HMG-CoA reductases, both of which have a N-terminus transmembrane spanning domain (1.6 kb). Thus, in a preferred embodiment, a yeast HMG-CoA reductase lacking at least part of this domain is utilized in the compositions and methods of the present invention.

VI. Geranylgeranyl Pyrophosphate

The BTS1 gene in *Saccharomyces cerevisiae* was cloned as a suppressor of a bet2-1 mutant, which is defective for the β-subunit of the type II geranylgeranyltransferase (Jiang et al., 1990). BTS1 suppresses a growth defect of bet2-1 whether expressed on a low (CEN) or multiple (2 um) copy vector. Furthermore, the BTS1 gene product demonstrates functional activity of a geranylgeranyl pyrophosphate (GGPP) synthase, such as functionally substituting for a bacterial GGPP synthase. The BET2 gene product is important for geranylgeranylation of a multitude of proteins in a variety of cellular processes, such as small GTP-binding proteins of the Ras superfamily and nuclear lamins. Up to 0.5% of cellular proteins are estimated to be prenylated which increases hydrophobicity and permits protein association with cellular membranes. Geranylgeranylation occurs from covalent attachment of all-trans geranylgeranyl diphosphate to proteins comprising terminal cysteines within CAAL, CC, or CXC sequence motifs. GGPP biosynthesis is critical for cell viability, and modifications in the prenylation pathway are contemplated to preferably include a reduced rate of GGPP consumption wherein the reduced rate is sufficient to maintain integrity of cellular homeostasis.

VII. Nucleic Acid-Based Expression Systems

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 1 lists several elements/promoters that may be employed, in the context of the present invention, to regulate the expression of a gene. This list is not intended to be exhaustive of all the possible elements involved in the promotion of expression but, merely, to be exemplary thereof. Table 2 provides examples of inducible elements, which are regions of a nucleic acid sequence that can be activated in response to a specific stimulus.

TABLE 1

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |

TABLE 1-continued

Promoter and/or Enhancer

| Promoter/Enhancer | References |
|---|---|
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Kiamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

In a preferred embodiment of the present invention, an inducible promoter is employed. In a preferred embodiment of the present invention, a GAL1 inducible promoter is employed. In other embodiments, a CUP1 or MET3 promoter is utilized. In *S. cerevisiae*, the copper metallothionein proteins encoded by CUP1 and CRS5 exhibit negative regulation by oxygen (Rae et al., 1999). Heterologous expression of genes under control of the CUP1 promoter yielded competitive transcriptional levels relative to the strong, constitutive GAPDH promoter and allowed successful characterization of a mammalian reductase (Hottiger et al., 1994; Poletti et al., 1996). MET3 promoters are also known in the art (Cherest et al., 1985; Mountain et al., 1991; Hampton et al., 1999).

In a specific embodiment, a constitutive promoter is utilized to regulate expression of a nucleic acid sequence of the present invention. Non-limiting examples of constitutive promoters include PGK and ADH, both of which are easily obtained using standard methods in the art such as PCR of genomic yeast DNA.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules undergo RNA splicing to remove introns from the primary transcripts. Vectors containing genomic eukaryotic sequences require donor and/or acceptor splicing sites to ensure proper processing of the transcript for protein expression. (See Chandler et al., 1997, herein incorporated by reference.)

5. Polyadenylation Signals

In expression, one typically includes a polyadenylation signal to effect proper polyadenylation of the transcript. The nature of the polyadenylation signal is not believed to be crucial to the successful practice of the invention, and/or any such sequence is employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements serve to enhance message levels and/or to minimize read through from the cassette into other sequences.

6. Origins of Replication

In order to propagate a vector in a host cell, it contains one or more origins of replication sites (often termed "ori"), which is a specific nucleic acid sequence at which replication is initiated. Alternatively an autonomously replicating sequence (ARS) is employed if the host cell is yeast. Further, yeast expression vectors containing an ARS are known that permit multiple copies of the vector in the same cell and, alternatively, there are yeast expression vectors that permit a single copy of the vector to reside in the cell (known as "single-copy").

7. Selectable and Screenable Markers

In certain embodiments of the invention, the cells contain nucleic acid construct of the present invention, a cell is identified in vitro or in vivo by including a marker in the expression vector. Such markers confer an identifiable change to the cell permitting easy identification of cells containing the expression vector. Generally, a selectable marker is one that confers a property that allows for selection. A positive selectable marker is one in which the presence of the marker allows for its selection, and a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Host Cells

As used herein, the terms "cell," "cell line," and "cell culture" may be used interchangeably. All of these terms also include their progeny, which is any and all subsequent generations. It is understood that all progeny are not necessarily identical due to deliberate or inadvertent mutations. In the context of expressing a heterologous nucleic acid sequence, "host cell" preferably refers to a eukaryotic yeast cell, and it includes a transformable organism that is capable of replicating a vector and/or expressing a heterologous gene encoded by a vector. A host cell is, and has been, used as a recipient for vectors. A host cell is "transfected" or "transformed," which refers to a process by which exogenous nucleic acid is transferred or introduced into the host cell. A transformed cell includes the primary subject cell and its progeny.

An appropriate host is employed by one of skill in the art based on the vector backbone and the desired result. A plasmid or cosmid, for example, is introduced into a yeast cell for replication of many vectors. Alternatively, a vector is introduced into a yeast cell for integration into the chromosome of the yeast cell.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

In a specific embodiment of the present invention, a vector is constructed and/or replicated in a bacterial host cell. Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® (Carlsbad, Calif.) and BACPACK™ BACULOVIRUS EXPRESSION SYSTEM FROM CLONTECH® (Palo Alto, Calif.).

Other examples of expression systems include STRATAGENE®'s (La Jolla, Calif.) COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides yeast expression systems called the *Pichia methanolica* Expression System and the *Pichia pastoris* Expression System, both of which are designed for high-level production of recombinant proteins in the methylotrophic yeast *Pichia methanolica* and *Pichia pastoris*, respectively. One of skill in the art would know how to express a vector, such as an expression construct, to produce a nucleic acid sequence or its cognate polypeptide, protein, or peptide.

EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus is considered to constitute preferred modes for its practice. However, those of skill in the art should, in light of the present disclosure, appreciate that many changes made in the specific embodiments which are disclosed and maintain a like or similar result without departing from the concept, spirit and scope of the invention. More specifically, it is apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Methods and Materials

Restriction enzymes, DNA polymerase I large (Klenow) fragment, T4 DNA polymerase, calf intestinal alkaline phosphatase, single-stranded binding protein, and M13K07 helper phage were purchased from New England BioLabs. Ligation reactions utilized Fast-Link DNA ligation kit purchased from Epicentre Technologies. Expand high fidelity polymerase kit used for PCR was purchased from Boehringer-Mannheim. Pfu polymerase and pGEM-T vector kit were purchased from Promega. pT7Blue T-vector was purchased from Novagen. Ex-Taq was purchased from Panvera. Zymolyase 100T was purchased from Seikagaku Corporation. Media ingredients were purchased from Fisher Biotech. Reagent chemicals were purchased from Sigma Chemical Company. Organic solvents were purchased from EM Science.

All *E. coli* cultures were cultivated in sterile Luria broth, LB. *E. coli* selective plates, LB-amp, were impregnated with ampicillin (250×stock: 25 mg/mL, filter sterilized) to a final concentration of 0.1 mg/mL. Blue-white recombinant *E. coli* selection required, in addition to ampicillin, 5-bromo-4-chloro-3-indoyl-β-D-galactoside (X-gal) added to the solid media to a final concentration of 20 µg/mL (200×stock: 200 mg X-Gal dissolved in 50 mL DMF).

The amino acid dropout mixes used were deficient in leucine, uracil, histidine, or tryptophan; the plasmid marker determined which amino acid mix was used in the preparation of the 2×Sc. The carbon sources were sugar solutions of dextrose (2×D: 20 g dextrose dissolved in 500 mL deionized water, then autoclaved 40 ml), or galactose (2×G: 20 g galactose dissolved in 500 mL deionized water, then autoclaved 40 min). The latter, galactose, was used to induce heterologous expression of recombinant genes and is, therefore, referred to as inducing media. Liquid media contained equal volumes of a nitrogen source and a carbon source. For solid yeast media, 7.5 g agar/500 mL was added to the carbon sources prior to sterilization. Plates for yeast cultivation contained a nitrogen source, a carbon source containing agar, and appropriate nutritional supplements, if needed. Supplements used were ergosterol (100×erg: 20 mg ergosterol dissolved in 5 mL ethanol and 5 mL Tween 80), hemin (100×hem: 13 mg hemin dissolved in 50% ethanol, 5 mM NaOH), cupric sulfate (0.1 M $CuSO_4$ stock: 638 mg cupric sulfate dissolved in 40 mL deionized water, filter sterilized), cholesterol (100×chol: 40 mg/mL prepared similarly to ergosterol supplement), nystatin (1 mg/mL dissolved in DMF; diluted with sterile deionized water), and 5-fluoroorotic acid (added directly to selective medium to a final concentration of 1 mg/mL).

Example 2

Production of GGPP in De Novo Sterol Biosynthesis

Figure 2:
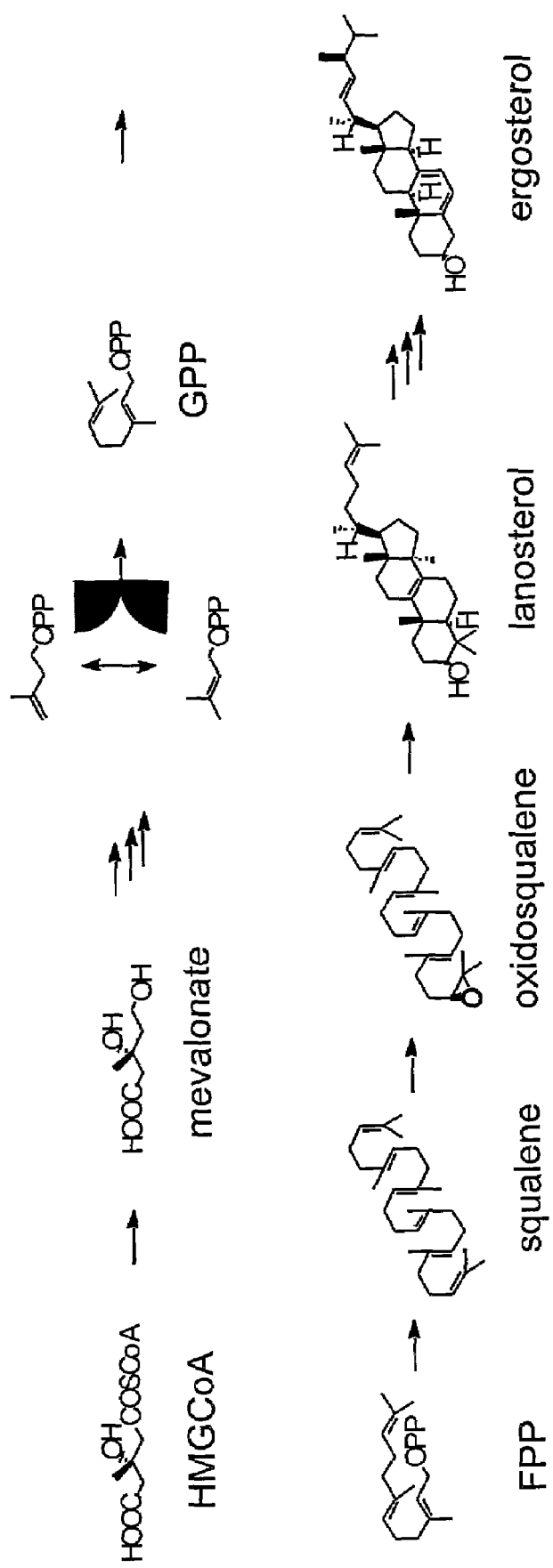
FIG. 2 illustrates de novo sterol biosynthesis native to *Saccharomyces cerevisiae*.
Figure 3:
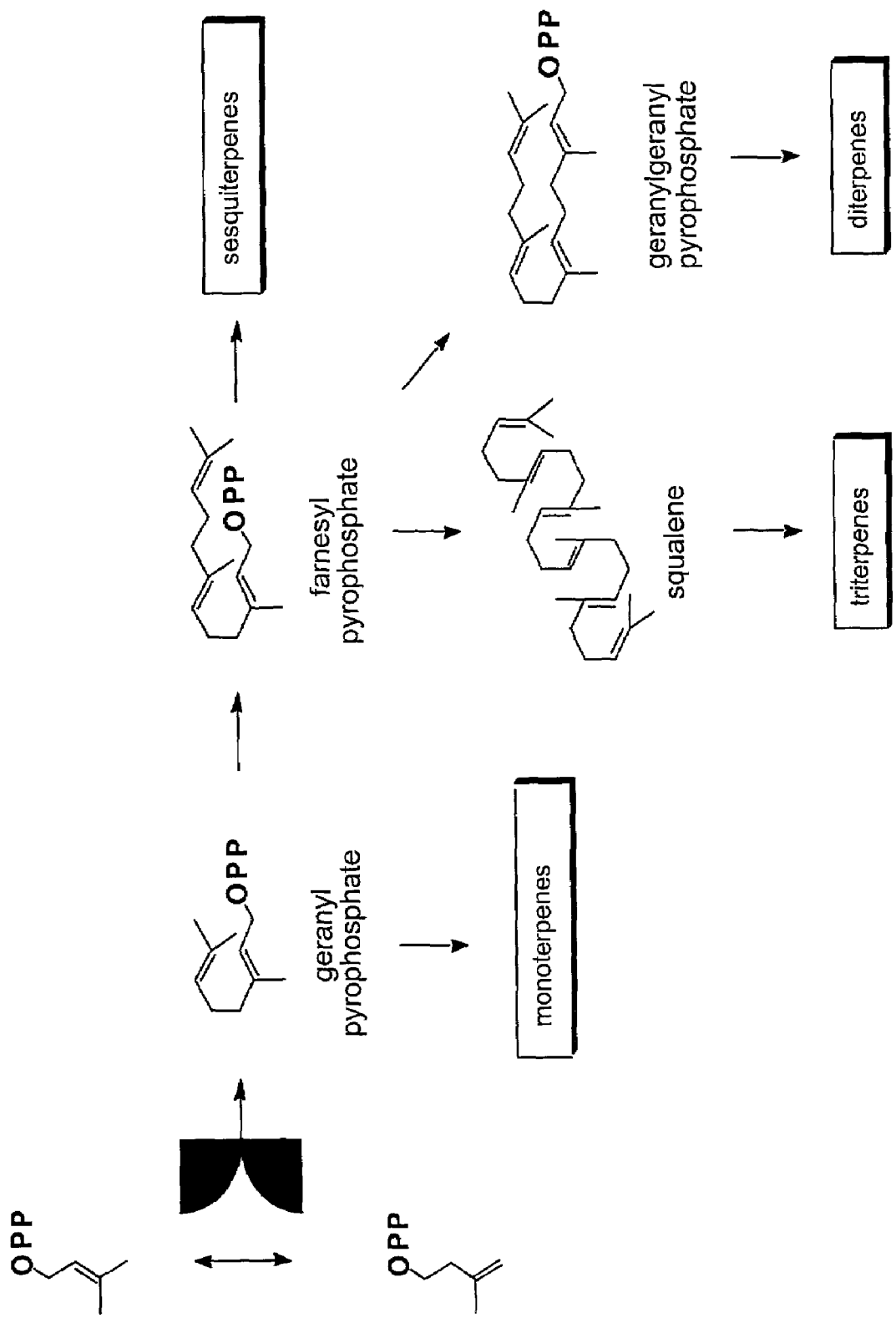
FIG. 3 illustrates terpene biosynthetic pathways resulting from sterol intermediates.

The amount of endogenous GGPP available in yeast having a native sterol biosynthetic pathway was established. FIG. 2 illustrates the main intermediates of de novo sterol biosynthesis in native yeast. FIG. 3 illustrates the terpene sub-classes and the sterol intermediates that serves as their biosynthetic precursors. Diterpenes are synthesized from (e.g., diterpene precursor) the metabolic intermediate geranylgeranyl pyrophosphate (GGPP).

Wild type yeast JBY575 (Alani et al., 1987) was transformed with a vector comprising a nucleic acid sequence encoding *A. grandis* abietadiene synthase (Mende et al., 1997). The culture media contained a polyaromatic resin that indiscriminately adsorbed molecules onto its surface. The induced culture was filtered and extracted to remove the diterpene product, and about 0.01 mg/L abietadiene (extrapolated from the internal standard longifolene at known concentrations) was observed by GC and GC/MS analyses. Because abietadiene relocated into the induction media, the elution of the adsorbed abietadiene from the resin or organic extraction of the media afforded the analytical sample. Control analyses included an uninduced culture of JBY575 [pEH9.0] and an induced culture of the same strain comprising vector lacking the abietadiene synthase, JBY575 [pRS426Gal]; neither control culture yielded detectable biosynthetic diterpene.

Example 3

Generation of GGPP-Synthesizing Yeast

Investigation of increasing GGPP biosynthesis included heterologous expression of the *S. cerevisiae* geranylgeranyl diphosphate synthase (BTS1) under transcriptional control of the inducible GAL1 promoter (Jiang et al., 1993).

The BTS1 nucleic acid sequence was isolated from λ phage received from ATCC using standard methods. Phage DNA containing *S. cerevisiae* BTS1 was digested with Xho1 and Kpn1 to release a 7 kb DNA fragment that subsequent to purification was ligated into pBluescript (II) KS$^+$ digested with the same two enzymes. Propagation in DH5α yielded pEH1.0. Excess sequence was removed from the insert of pEH1.0 to yield pEH1.1.

The native promoter of BTS1 was removed by installing a Sal1 site immediately upstream of the start codon by site-directed mutagenesis employing the oligonucleotide sequence GP5S: 5'-TATCTTGGCCTCCAT<u>GTCGAC</u>TCCAGACTCGTAAAC-3' (SEQ ID NO:408) and standard methodologies known in the art. The resulting plasmid was named pEH1.2 and confirmed by sequencing. The nucleic acid sequence encoding BTS1 was removed by double digestion of pEH1.2 with Sal1 and Not1 and inserted into yeast expression vectors pRS305Gal and pRS426Gal to afford plasmids pEH1.3 and pEH1.4, respectively.

Figure 4:
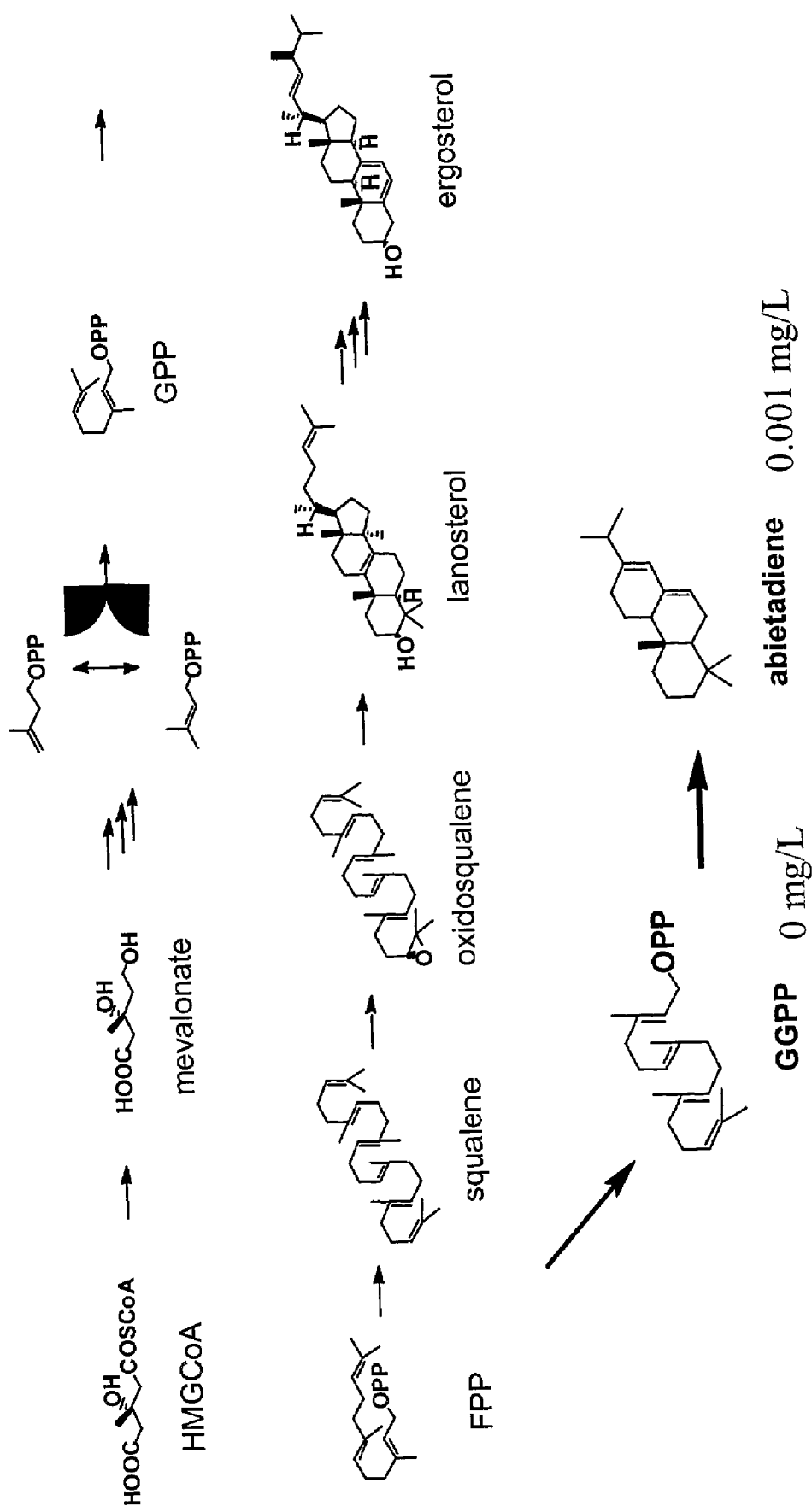
FIG. 4 illustrates diterpene and diterpene production in wild-type yeast.
Figure 5:
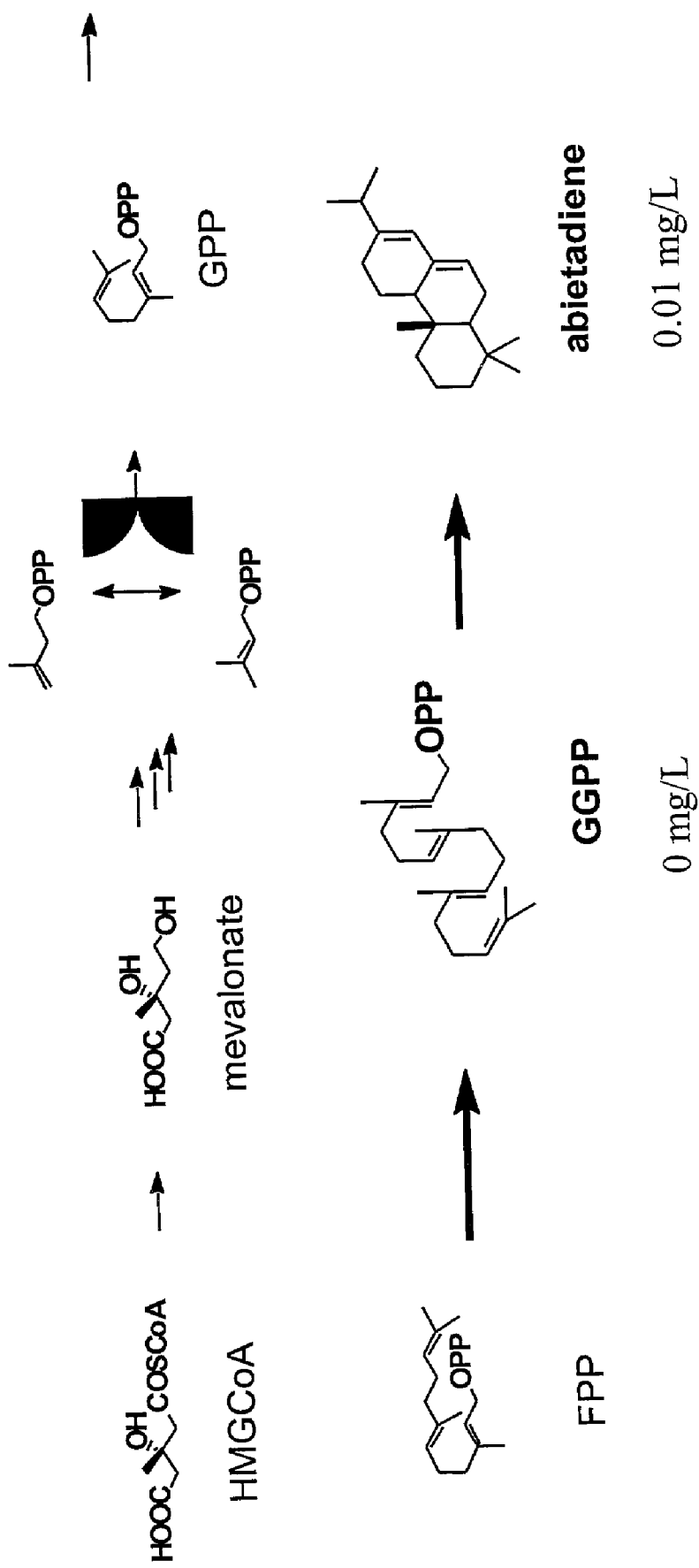
FIG. 5 illustrates GGPP and abietadiene production in yeast comprising an overexpressed BTS1 nucleic acid sequence.

JBY575 (MATa ura3-52 trp1-Δ63 leu2-3,112 his3-Δ200 ade2 Gal$^+$) was transformed with BstE II digested pEH1.3 and selected on 2% glucose, 1.5% agar, and 2% synthetic complete media lacking leucine by growing at 30° C. until colonies were observed (~2–3 days). A second round of selection on the same medium yielded EHY1 (MATa pGAL1-BTS1::LEU2 ura3-52 trp1-Δ63 leu2-3,112 his3-Δ200 ade2 Gal$^+$), which was transformed with pEH9.0. Induced cultures of EHY1[pEH9.0] afforded approximately 0.05–0.10 mg/L detectable abietadiene. FIG. 4 illustrates the engineered metabolic pathway of EHY1 The uninduced culture of EHY1[pEH9.0] exhibited no biosynthetic abietadiene indicating that the acquired ability to manufacture Bts1p in response to galactose provided in the growth medium led to increased production of diterpene and consequently diterpene precursor.

The amount of diterpene observed was recognized as an indirect indicator of the increased amount of endogenous GGPP. The indirect measure has the advantage that accumulation of high amounts of GGPP does not effect inherent regulation of sterol biosynthesis. In a specific example, abietadiene was generated by adding a nucleic acid that encodes abietadiene synthase (SEQ ID NO:365; Funk and Croteau, 1994) to the cell. The sequence was plasmid-borne and retained in the cell by selection.

Example 4

Altering Metabolic Flux to Produce Diterpenes

Increasing metabolic flux through the sterol biosynthetic pathway to increase the biosynthetic rate of a diterpene precursor GGPP was demonstrated. The HMG-CoA reductase (HMGR) enzyme effects reduction of HMG-CoA to mevalonic acid and is known to be a rate-limiting transformation in sterol biosynthesis. One mechanism employed to increase metabolic flux involved increasing the reaction rate of a rate-determining reaction.

The *S. cerevisiae* HMG1 was obtained by a PCR strategy to include a nucleic acid sequence encoding amino acids 545–1054 and a start codon (ATG) in-frame with the first coding residue. The removal of the transmembrane spanning domains was effected by installing a Sal I site at the desired splice site. The HMG1 was processed using standard methods to produce a soluble form of the HMG-CoA reductase. Yeast shuttle vectors pRS305Gal and pRS314Gal comprising the nucleic acid sequence encoding the soluble form of HMG1 were named pEH12.1 and pEH12.2, respectively. The plasmids differed by their selectable markers (LEU2 and TRP1, respectively) and their type of expression vector (integrative and single-copy, respectively). Both pEH12.1 and pEH12.2 further comprised the GAL1 inducible promoter by which expression of the soluble form of HMG1 was controlled.

Recombinant yeast strain EHY1 was cotransformed with pEH12.2 and pEH9.0 and maintained on selective media. The resulting strain, EHY1[pEH12.2][pEH9.0], produced approximately 1.0 mg/L abietadiene. Unexpectedly, geranylgeraniol (GGOH) was also detected in the induced culture of EHY1[pEH12.2][pEH9.0] and suggested that the diterpene synthase represented a rate-limiting step in the installed diterpene pathway. A skilled artisan recognizes that metabolic pathways are regulated, and the observed alteration in GGPP biosynthesis is vulnerable to inducing such regulation. Thus, alternatively, the observed GGOH suggests that a regulatory event has been initiated to achieve homeostatic levels of GGPP. The excess GGPP was readily hydrolyzed in the cytoplasm to produce intracellular GGOH, a known cytotoxin, which is then excreted from the cell. Previous observations identifying sterol intermediates in the growth media of cultured cells suggested that passive diffusion through the lipid bilayer lay cause for the export out of the cell.

In another specific embodiment, *Arabidopsis thaliana* HMG-CoA reductase nucleic acid sequence (such as SEQ ID NO:251, SEQ ID NO:267 or SEQ ID NO:468), which contains only two transmembrane spanning domains rather than seven domains present in the yeast primary sequence, is incorporated into the *S. cerevisiae* genome under control of a promoter, preferably an inducible promoter.

Example 5

Production of Geranylgeraniol

Figure 8:
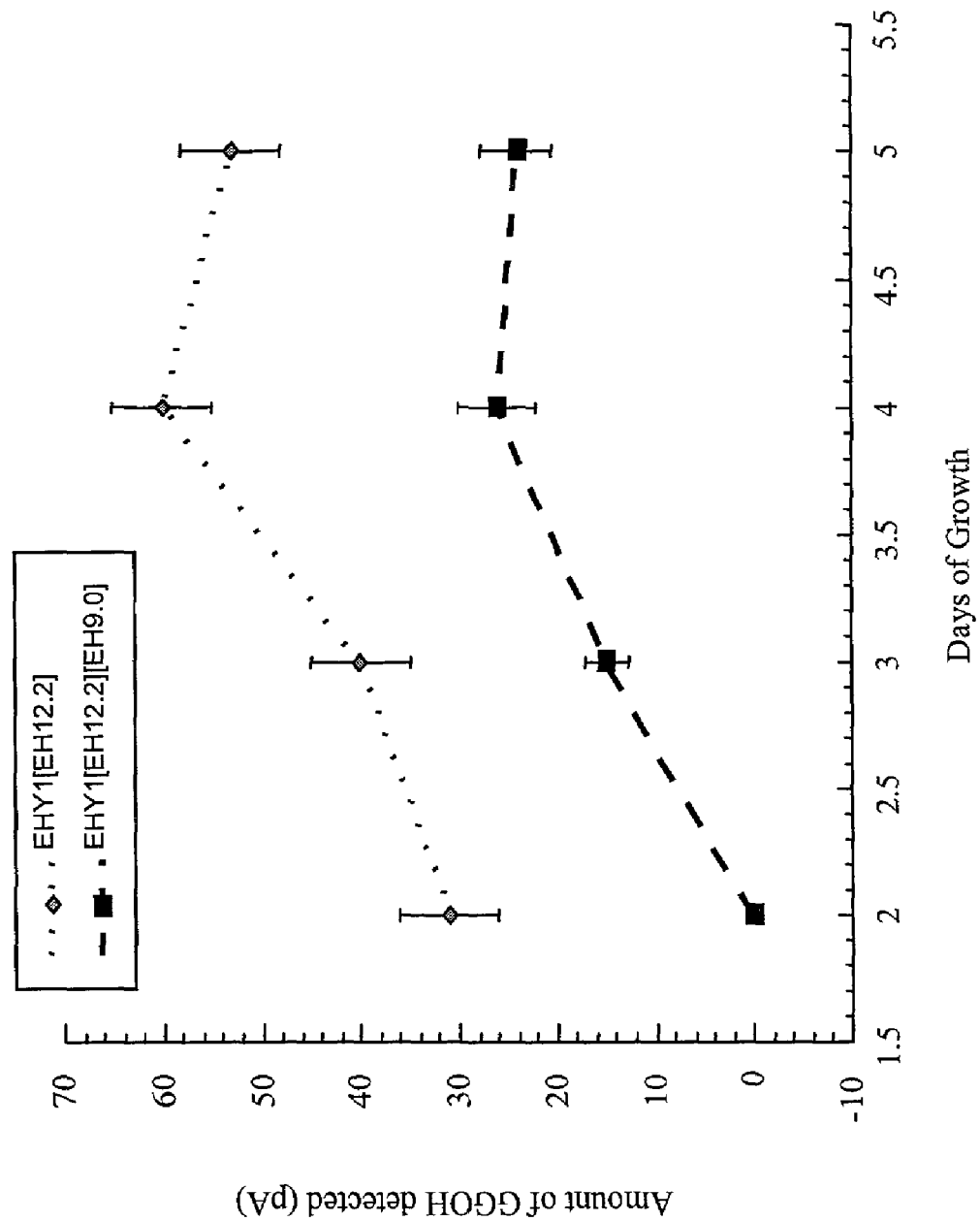
FIG. 8 illustrates the amount of geranylgeraniol production in a cell grown in 2% galactose having an overexpressed BTS1 and HMG-CoA reductase, with and without an overexpressed diterpene synthase.

Geranylgeranyl pyrophosphate is an unstable molecule due to the lability of the pyrophosphate moiety. The instability directly effects the cost of commercially available GGPP. The organism of the present invention provides an alternative to producing GGPP and employing GGPP in the synthesis of diterpenes in vivo. Further, the organism provides GGOH, an important synthetic material that is too costly for large scale commercial use. FIG. 8 illustrates the amount of geranylgeraniol production in a cell of the present invention grown in media comprising 2% galactose. The dotted line is the GGOH production in yeast comprising a chromosomal nucleic acid sequence encoding BTS1 under control of the GAL1 promoter and the plasmid-borne nucleic acid sequence encoding the soluble form of HMG1 under the control of the GAL1 promoter. The broken line is the same strain further comprising abietadiene synthase under control of the GAL1 promoter (EHY1[pEH12.2] [pEH9.0]).

Peak areas were obtained by GC analyses and are reported in picoamps (pA), which indicates the abundance of analyte as measured electronically by the flame-ionization detector. The Day 2 induced culture of EHY1[pEH12.2][pEH9.0] produced undetectable levels of GGOH. However, GGOH production increased between Days 2 and 4. Growing beyond Day 4 afforded no increase in GGOH suggesting that GGPP biosynthesis, measured indirectly as the excreted alcohol derivative, is contingent on the metabolic flux of the sterol biosynthetic pathway, which slows in conjunction with mitotic growth. The data indicate that the recombinant strains lacking a diterpene synthase, EHY1[pEH12.2], biosynthesized 40–60% more GGOH than the same strain further comprising the diterpene synthase.

Because strict regulation exists to maintain appropriate sterol levels, it is likely that the disturbance of the increased intracellular levels of GGPP triggered a mechanism responsible for maintaining homeostasis with regards to the rate FPP is diverted to GGPP, the intracellular GGPP levels, or the intracellular GGOH levels. The unexpected GGOH accumulation represents an unnatural occurrence in yeast cellular metabolism, and a reasonable cellular response is to counteract the perturbation.

Example 6

Effect of UPC2-1

The upc2-1 allele was incorporated to indirectly effect the metabolic flux of sterol biosynthesis and provide for an increased production of GGPP, GGOH and diterpene. A genetic cross by standard means in the art was performed to incorporate the upc2-1 allele into strains of different mating type having BTS1 and the soluble form of HMG-CoA reductase, both under control of an inducible promoter. That is, crosses were performed in lieu of plasmid transformations to conserve selectable markers in the host cell.

Strains carrying the upc2-1 allele, CJ2-A and SC2-1C were obtained as a generous gift from Prof. L. Parks, and genetically crossed to EHY1. The resulting strains were named EHY18 (MATa pGAL1-BTS1::his pGAL1-trHMG1::LEU2 upc2-1 ura3-52 leu2-3,112 trp1-Δ63 his3-Δ200 ade2 Gal+) and EHY19 (MATα pGAL1-BTS1::his pGAL1-trHMG1::LEU2 upc2-1 ura3-52 leu2-3,112 trp1-Δ63 his3-Δ200 ade2 Gal+). Both strains were transformed with pEH9.0 and grown in inducing media to observe the amount of biosynthesized diterpene. Both JBY575[pEH9.0] and EHY1[pEH12.2][pEH9.0] were analyzed to establish the effect of upc2-1 on diterpene and diterpene precursor production. The analyze peak corresponding to abietadiene indicated an increase of nearly three-fold in diterpene production in EHY18[pEH9.0] as compared to EHY1 [pEH12.2][pEH9.0] and about 300-fold increase in diterpene production relative to JBY575[pEH9.0]. The uninduced control cultures of each strain demonstrated undetectable levels of abietadiene by GC.

Example 7

Optimization of Variable Parameters

The analytical method employed in the present invention improved compound recovery as compared to extraction of the cell lysate and culture media. Hydrophobic resin has been used to isolate secondary metabolites from cultures in an effort to sequester the compounds, thereby thwarting degradation. In the present invention, a porous polyaromatic resin was sterilized and added to the growth medium prior to the induction phase.

The ratio employed was about 5% (w/v) of the induced culture. The preparation of the resin included wetting with alcohol followed by sterilization. A skilled artisan is aware of methods to determine optimal weight-to-volume ratios by considering, for example, diterpene and diterpene precursor production levels relative to resin adsorbent capacity, incubation and/or growth time and the ability of the resin to adsorb and/or absorb nutrients from the medium. The wetting procedure was examined with methanol, the recommended solvent, and ethanol; better tolerated by yeast than methanol. No effect on diterpene production was observed between the use of different wetting solvents.

Optimization of the dilution factor (inoculum volume) and induction time in the presence of the resin was performed. The concentrated inoculum (1:20 dilution factor) yielded no obvious advantages to a more dilute induction volume (1:1000); therefore, the latter was used to allow for additional generations under inducing conditions. Induction time was tested at 48, 72, 96, and 105 hours. The yields of detectable diterpene benefited from longer induction times. During these experiments, the culture media and the cell lysate of cultures grown with and without resin were also extracted and analyzed for diterpenes and diterpene precursors.

The effect of the resin on the optical densities of induced cultures was determined. EHY1[pEH12.2][pEH9.0] was induced for 48 h in the presence and absence of resin. The optical density of the culture devoid of resin achieved twice the optical density of the culture containing resin. Although the induced culture lacking resin produced a higher cell mass less abietadiene was removed by extraction. In contrast, the same strain grown in the presence of the resin achieved a relatively lower cell density and produced about 1 mg/L abietadiene in vivo. The filtrate removed from the resin was also extracted to determine the efficiency with which the excreted abietadiene absorbed to the resin. An additional 15% of the total abietadiene detected from the resin eluent was detected in the extracted culture media. To compensate for binding inefficiency all samples were grown for four days unless otherwise specified. Longer incubation times did not significantly increase optical density measurements. A control of growth media containing resin but no cells was analyzed in order to assign the background contributed by the resin.

The incorporation of the resin functioned as a means to remove the excreted hydrophobic compounds of biosynthetic origin and effected nearly a seven-fold increase in recovered diterpene and diterpene precursors. In a specific embodiment, the growth of the cell is affected by the amount of GGPP accumulated, particularly in embodiments affecting prenylation. These effects occur if a toxic diterpene hydrocarbon is produced at a faster rate than the rate of secretion to the medium. However, ready transport of the accumulated diterpene precursor, GGPP hydrolyzed to GGOH, has been observed. Furthermore, the surface capacity and chemical characteristics of the adsorbent resin effects recovery. Modifying the type of resin the ratio employed in the medium is within the skill of one with ordinary skill in the art. Furthermore, a skilled artisan is aware of growth conditions or alterations within the cell itself to circumvent difficulties as a result of deleterious saturation or toxic levels.

Example 8

Abietadiene Production Versus Galactose Concentration

The production of abietadiene, which reflects the production levels of GGPP, is influenced by the amount of inducer available. Induced cultures of EHY18[pEH9.0] grown in medium comprising various initial galactose concentrations were tested. Specifically, induced cultures containing 2%, 4%, and 8% galactose concentrations were analyzed in triplicate. The same strain comprising the GGPP synthase, the soluble form of HMG1 and the upc2-1 allele but lacking the diterpene cyclase (EHY18) was grown under similar inducing conditions to determine background. No diterpene was detected in the strain lacking the diterpene cyclase.

Abietadiene production in EHY18[pEH9.0] reached a maximum in the 4% galactose culture by increasing nearly two-fold over the amount of abietadiene detected in the 2% galactose culture. The 8% galactose culture did not induce a significant increase in the amount of abietadiene detected as compared to the 4% galactose culture. The experiment indicated that a two-fold increase in diterpene production resulted from cultivating with increased amounts of inducer (i.e., galactose).

The diterpene production in the compositions of the present invention effected growth rates and saturation levels. Optical densities of induced cultures expressing abietadiene synthase, EHY18[pEH9.0], were compared to optical densities of induced cultures lacking the cyclase activity, EHY18. The induced EHY18 and EHY18[pEH9.0] cultures grown in various galactose compositions were measured ($\lambda$=600 nm) for cell density prior to sample processing. The optical density measurements of EHY18 and EHY18 [pEH9.0] were significantly increased in 4% inducing media relative to 2% inducing media. Comparing measurements of the two strains in all galactose concentrations suggested that consumption of the diterpene precursors by an incorporated diterpene synthase effected higher optical densities.

Example 9

Methods of Analysis

Removal of diterpene and diterpene precursors was demonstrated using both organic extraction, and a modified procedure as provided herein based on that described in Hara et al. (1989).

Terpene Accumulation Assay

Small-scale analysis of terpene accumulation involved growing an uninduced culture of a strain at 30° C. in 5 mL dextrose and synthetic complete media lacking uracil. Those strains bearing plasmid-borne nucleic acid sequences were grown at 30° C. in 5 mL dextrose and synthetic complete media with appropriate selection. The saturated culture was harvested by centrifugation (1500×g, 3 min); the cell pellet was rinsed twice with 500 µL sterile deionized water to remove residual media. The cells were then resuspended in 5 mL sterile deionized water. This suspension was used as inoculum in a 1:1000-fold dilution (5 µL) into 5 mL induction media. The induction media contained equal volumes of 2×galactose (G) and 2×synthetic complete media (SC) lacking uracil added to a 25 mL Corex tube pre-prepared with HP-20 diaion resin (~0.35 g wet resin was weighed into a clean Corex tube then overlaid with methanol and allowed to incubate for 15 min; methanol was removed and the resin was rinsed twice with deionized water. The resin was overlaid with 600 µL deionized water and autoclaved 15 min).

The saturated cultures were filtered through a Kontes chromatograph column (2.8×25 cm) to remove cellular debris and growth media. The captured resin was rinsed with copious amounts of water then eluted thrice with 2 mL ethanol. Ethanolic eluents were combined and extracted with pentane or hexane. The organic extracts were combined and dried at ambient temperatures under a nitrogen stream.

The large-scale assays were performed as described for the small-scale assay except the filtering apparatus varied. Large glass chromatograph columns (3×40 cm) were used to filter cells and growth media from the resin. Elution of the organics from the resin was achieved by passing 300–500 mL ethanol over the resin. The eluent was then extracted thrice with pentane. The combined organic extracts were dried over $MgSO_4$, condensed in vacuo, and stored under nitrogen at −20° C.

Analytical Instrumentation

GC analysis was performed on an HP 6890 series equipped with an Rtx-5 capillary column (30 m×0.25 mm i.d., 0.1 µm df), a FID detection system with a split ratio of 1:40 (helium was used as carrier). The oven utlized program with relative to the size of the terpene molecule under observation. Sesquiterpene detection employs the following oven program: 70° C. for 1 min, 15° C./min increase to 250° C. and hold for 3 min. Both injector and detector were set to 250° C. Diterpenes were separated for detection using a temperature program with an initial temperature of 150° C. for 5 min, then 5° C./min increase to 250° C. and hold for 5 min. Injector and detector temperatures were held at 250° C. Longifolene (0.25 mg/mL) served as the internal standard. Standards for longifolene, geraniol, farnesol, and geranylgeraniol were obtained from Sigma Chemical Company (St. Louis, Mo.).

GC/MS analysis was performed on VG ZAB-HF GC-MS, and the GC oven program was utilized. The capillary column was purchased from J&W Scientific (Folsom, Calif.) (DB-5 ms (60 m×0.25 mm i.d., 0.1 mm df)). Transfer lines were set to the injector temperature. Ionization by electron-impact (EI) was achieved at 70 eV with a scan time of 4.0 sec.

Example 10

Characterization of Diterpene and Diterpene Precursors

Figure 9:
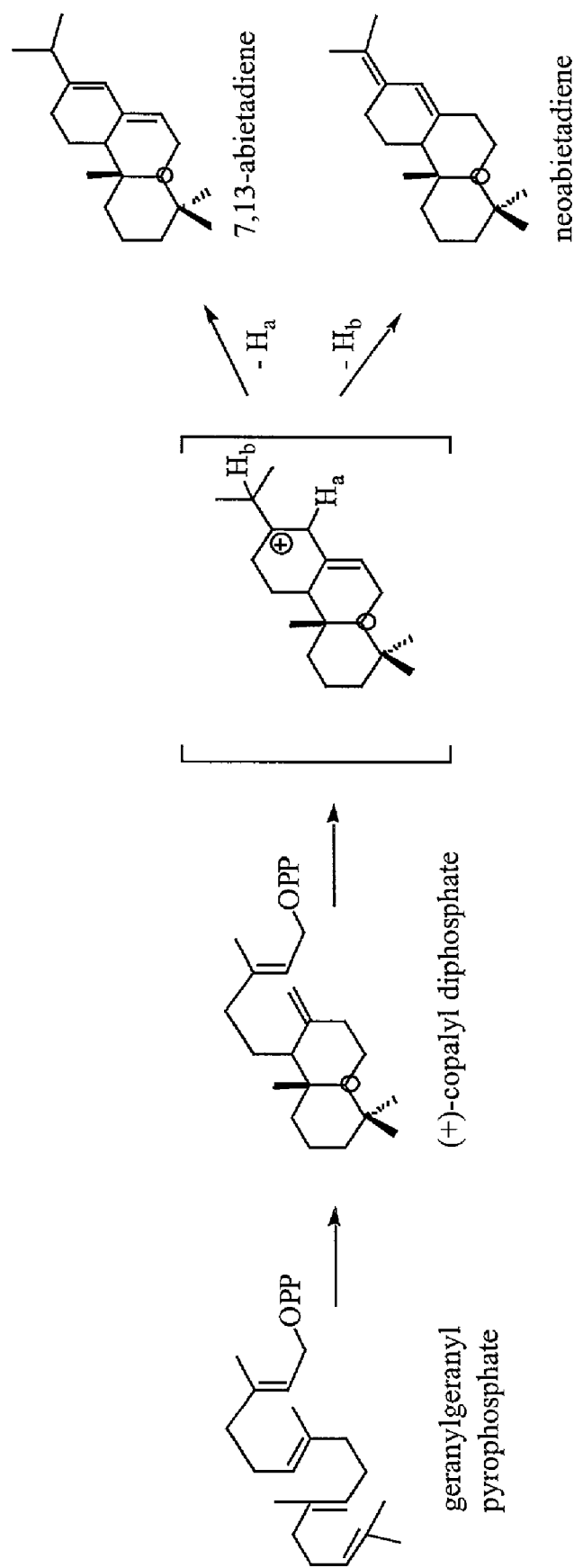
FIG. 9 illustrates the catalytic mechanism of a diterpene cyclase.

A 1-L induced culture of EHY18[pEH9.0] was grown under conditions wherein diterpene and diterpene precursors were produced. The resin eluent was purified for the major product (5 mg, 85% pure) and confirmed by $^1$H-NMR to be biosynthetic 7,13-abietadiene (FIG. 9). The abietadiene fraction contained at least three biosynthetic products possessing m/z=272 by GC/MS analysis. The major compound (97% relative ratio) was confirmed to be 7,13-abietadiene. An isomer (3% relative ratio) of biosynthetic origin produced a fragmentation pattern that corresponded to neoabietadiene. In addition, NMR data demonstrated an upfield methyl singlet ($\delta$ 0.629 ppm) indicated the presence of another isomer possessing, most likely, a double bond at the C-7 position. No evidence of levopimaradiene was found despite significant production of this isomer detected upon expression of a truncated abietadiene synthase and in vitro incubation with substrate (Ravn et al., 1998).

Example 11

Altering Sterol Metabolism Upstream of GGPP

The unicellular organisms of the present invention demonstrate improved production of diterpenes and diterpene precursors in vivo. Efforts to increase the production yields further comprised minimizing the effect of competing biosynthetic processes on endogenous GGPP levels. Geranylgeranyl pyrophosphate results from the head-to-tail condensation of isopentenyl pyrophosphate and farnesyl pyrophosphate (FPP). However, the majority of FPP is consumed in biosynthesis of squalene.

The formation of squalene results from the head-to-head condensation of two molecules of FPP; the two-step transformation is catalyzed by squalene synthase and constitutes a branch point in the sterol biosynthetic pathway. Commonly, branch point transformations represent highly regulated steps in a metabolic pathway and, thus, deletion of such are avoided. Squalene synthase, also referred to as farnesyl diphosphate:farnesyl diphosphate farnesyl-transferase, is encoded by ERG9 in yeast and is a likely regulatory site for sterol biosynthesis. It is known that squalene synthase is inhibited by a variety of compounds, including analogs of FPP (Corey and Volante, 1976; Ortiz de Montellano et al., 1977; Bertolino et al., 1978). Intermediates between FPP and squalene are well known in the art and are also the target of inhibition (Rilling, 1966; Popjak et al., 1969; Epstein and Rilling, 1970). Examples of ERG9 inhibitors include squalestatin I, farnesylamine, dodecylamine, and cis-N-farnesyl aminoethyl morpholine.

In a specific embodiment, at least one ERG9 (squalene synthase) (GenBank Accession No. X59959; SEQ ID NO:409) modification is generated by standard means in the art to create a "bottleneck" in the pathway, thereby permitting the shuttling of increased amounts of FPP to the bioengineered diterpene pathway. One means to partially block a transformation is achieved by employing a temperature-sensitive mutation which allows examination of impaired enzymatic activity without the adverse effect of completely blocking metabolism. Temperature-sensitive mutations weaken an enzyme's secondary structure. The resultant protein becomes especially sensitive to thermal denaturation, thereby rendering its activity temperature-sensitive. A temperature-sensitive ERG9 mutation (Karst et al., 1971) was incorporated by genetic cross into the yeast comprising a chromosomal nucleic acid sequence encoding a GGPP synthase under the control of an inducible promoter. A strain comprising the erg9-1 temperature-sensitive mutation was purchased from American Type Culture Collection (ATCC 64031) and tetrads from the genetic crosses were selected by observing growth rate at various temperatures as compared to the control strain EHY1.

Optimal growth temperature was determined on solid media and indicated that above 36° C. was lethal to the engineered yeast comprising the erg9-1 temperature-sensitive mutation. The diterpene and diterpene precursor production of the strains comprising the erg9-1 allele were referenced to the production yields observed at 30° C. incubation temperature.

Strains further comprising the chromosomal nucleic acid sequence encoding the GGPP synthase under control of an inducible promoter benefited from longer incubation times. An initial 24 h incubation at 30° C. was determined to be advantageous to diterpene production in all strains comprising the temperature-sensitive erg9-1 allele.

The strain comprising the erg9-1 allele, the upc2-1 allele, the chromosomal nucleic acid sequence encoding the GGPP synthase under control of the inducible promoter, the plasmid-borne nucleic acid sequence encoding the soluble form of HMG1 under control of an inducible promoter and the plasmid-borne nucleic acid sequence encoding the diterpene synthase under control of an inducible promoter yielded an increase in detectable GGOH relative to the control strain suggesting that an increase in the native metabolic rate of sterol biosynthesis is critical for diterpene precursor accumulation. However, the same strain produced lower levels of detectable abietadiene than the analogous strain lacking the nucleic acid sequence encoding the soluble form of HMG1. Negligible amounts of diterpene and diterpene precursors were produced in the strain comprising the erg9-1 allele, the nucleic acid sequence encoding the GGPP synthase and the nucleic acid sequence encoding the diterpene synthase.

Example 12

Sterol Production in Metabolically Engineered Yeast

Determining the amount of ergosterol biosynthesized in the engineered strains of the present invention indicated that metabolic flux of the sterol biosynthetic pathway is increased as compared to metabolic flux of native sterol biosynthesis (Table 3). Ergosterol is the end product of sterol biosynthesis in yeast. Quantifying the amount of ergosterol in the organisms modified to produce diterpenes and diterpene precursors allows one of ordinary skill on the art to monitor the effect of the genetic modifications on sterol metabolism as a whole. This is critical to maintaining a healthy and stabile engineered organism. Induced cultures of JBY575[pEH9.0], EHY1[pEH12.2][pEH9.0], EHY18 [pEH9.0], and EHY32[pEH9.0] were evaluated for total ergosterol content. Saponification of 50 mL induced cultures grown without resin afforded approximately 1 mg total sterol. Reaction products were silylated, analyzed by GC and compared to silylated ergosterol prepared at known concentrations. Native yeast expressing the diterpene synthase under the control of an inducible promoter established the ergosterol level for an intact sterol biosynthetic pathway. Comparatively, a 4.5-fold increase in ergosterol levels were observed in the yeast overexpressing the soluble form of HMG1 under control of the GAL1 promoter and comprising the upc2-1 allele.

Other means by which an end product is isolated and/or analyzed are known in the art. For example, accumulating sterol is often esterified for storage, and thus a reaction was employed that allowed hydrolysis of accumulating ergosteryl ester and subsequent detection of both free and esteri fied ergosterol. The increase in ergosterol content demonstrated by EHY18[pEH9.0] suggests that the rate of sterol biosynthesis therein is producing a diterpene precursor in an amount sufficient for circumventing to diterpene production in vivo beyond that which is exploited by the modifications described herein. This suggests that further modifications, such as those described in EXAMPLE 13, to divert the accumulating pool of diterpene precursor are advantageous to diterpene production yields.

Example 13

Inhibition of Other FPP-Associated Pathways

It is known that intermediates such as GGPP and FPP are shared by multiple pathways (Keller, 1996). In a preferred embodiment, at least one other metabolic pathway associated with FPP is modified so that increased or enhanced flux occurs into the FPP to GGPP bioengineered pathway. In one embodiment of the present invention, modification is defined as incomplete inhibition, and in an alternative embodiment modification is defined as complete inhibition. In a preferred embodiment, the endogenous FPP-associated pathway(s) is not modified to the extent that said modification(s) is deleterious to the cell. Alternatively, the pathway is modified to a deleterious extent, but the required product (s) is provided by another means. In specific embodiments, the activity of a particular enzyme and/or the expression of the nucleic acid sequence which encodes it is decreased or downregulated, respectively. In other embodiments, there is an alteration in a nucleic acid sequence which encodes a particular enzyme, there is an alteration in expression of a nucleic acid sequence which encodes a particular enzyme, there is an alteration in translation or proteolysis of the enzyme, or a combination thereof. The term "alteration" as used herein is defined as a change in the function of a nucleic sequence and/or the amino acid sequence which is encoded by it. Non-limiting examples of alterations include a mutation, such as a point mutation, frameshift mutation, nonsense mutation, temperature-sensitive mutation, a deletion, an inversion, a change in regulation of a nucleic acid sequence through modification of regulatory elements, or a combination thereof.

In one embodiment of the present invention, an inducible promoter was inserted onto a chromosome such that the promoter was operatively linked to the chromosomal squalene synthase in S. cerevisiae. The inducible promoter, CUP1, has been described as regulating competitive transcriptional levels relative to the constitutive GAPDH promoter and has been employed in functional gene characterization. The CUP1 promoter induces expression as a function of intracellular copper content, and thus in a specific embodiment, an inducer is a copper salt, and preferably cupric sulfate.

A skilled artisan is aware that modification of the metabolic pathway is achieved by negatively affecting enzyme activity, either partially or completely, or by decreasing expression of the nucleotide sequence which encodes the enzyme, all of which employ standard and well known methods in the art in yeast. That is, inhibition of steps in metabolic pathways are accomplished, for example, via genetics, such as by generating a mutation or deletion of the nucleic acid sequence which encodes the enzyme, by downregulating the expression of the nucleic acid sequence which encodes the enzyme, or by administering to the cell an inhibitor of the enzyme function and/or activity. In another embodiment, different growth parameters are altered to attain at least one growing condition to decrease activity of a sensitive enzyme. Such parameters include oxygen availability, temperature, carbon source and amount, and the like.

Potential target sites include inhibition of enzymes at any point in the pathway, but preferably at a transformation that consumes FPP, and more preferably consumes FPP as a substrate. Examples of such pathways include the squalene synthase pathway and the pathway which converts high-molecular weight precursors of dolichols and ubiquinones, and the prenylation pathway.

In one embodiment, a sterol biosynthetic pathway is inhibited, such as in the squalene synthase pathway, to increase FPP flux into the engineered GGPP biosynthesis pathway. Similarly, ERG1 (squalene epoxidase) (GenBank Accession No. M64994; SEQ ID NO:410) consumes squalene for sterol biosynthesis and such is a target for separate or additional alteration to increase levels of FPP for GGPP biosynthesis. In alternative embodiments additional enzymatic steps are modified, wherein the enzymatic steps are known in the art and/or are identified by standard screens known in the art, such as those described herein. Other sites contemplated for modification of the squalene synthase pathway include squalene epoxidase (ERG1) and/or lanosterol synthase (ERG7) (GenBank Accession No. U04841; SEQ ID NO:411).

Example 14 upc2-1 Alternatives

In a specific embodiment, there is a yeast cell for producing GGPP in vivo, comprising a nucleic acid sequence encoding a GGPP synthase, a nucleic acid sequence encoding a soluble form of HMG-CoA reductase and a nucleic acid sequence that confers an increase in sterol metabolic flux as compared to native sterol metabolic flux levels. The increase in sterol metabolic flux includes increased production in vivo of acetate, mevalonate, hydroxymethylglutaryl coenzyme A, isopentenyl pyrophosphate, dimethylallyl pyrophosphate, geranyl pyrophosphate, farnesyl pyrophosphate and geranylgeranyl pyrophosphate. A nucleic acid sequence that confers an increase in the production of these intermediates effect the sterol metabolic flux to the extent that diterpene and diterpene precursor production is increased as compared to native sterol metabolic flux levels.

In another specific embodiment, there is a yeast cell for producing a diterpene in vivo, comprising an exogenous nucleic acid sequence encoding GGPP synthase and an exogenous nucleic acid sequence encoding a diterpene synthase. In a further embodiment, the cell further comprises an exogenous nucleic acid sequence encoding a HMG-CoA reductase. In a preferred embodiment, the HMG-CoA reductase is containing a deletion wherein the deletion affords a more soluble form of the reductase as compared to the native reductase. In a further embodiment, the cell further comprises an exogenous nucleic acid sequence that encodes a gene product which confers to said cell an increase in sterol biosynthesis. In yet another specific embodiment, the cell further comprises an exogenous nucleic acid sequence the encodes a gene product which confers to said cell sterol importation under aerobic conditions. Thus, although the upc2-1 allele is utilized in the compositions and methods of the present invention for increasing sterol biosynthesis (increasing sterol metabolic flux), the allele is reported to additionally overcome control of the sterol import/export mechanism. In an alternative embodiment, two separate alleles which confer both phenotypes, or a different single allele which confers both phenotypes. For instance, a genetic mutation in the heme biosynthetic pathway mimics the effect of anaerobic growth and permits importation of exogenous sterols (Parks and Casey, 1995).

Alternatively, a sterol uptake gene (SUT1) has been described as permitting importation of exogenous sterols (Karst et al., 1995). And, more recently this same gene is purported to upregulate sterol synthesis in aerobically grown *S. cerevisae* (Ness et al., 2001). Thus, the observed ability for SUT1 to confer an increase in sterol synthesis suggests that this gene product increases sterol metabolic flux levels as compared to native sterol flux levels. The ability to overcome the sterol import/export mechanism affords the recombinant organism particular advantages in that further modifications to increase metabolic flux, diterpene precursor and/or diterpene production include targeting sites along the pathway that effect adversely sterol flux, such as highly regulated enzymatic steps (i.e., squalene synthase).

Example 15

Methods to Screen for Other Diterpene Synthases

In another embodiment of the present invention, there is a method of isolating a diterpene synthase, comprising the steps of growing a plurality of cells which express a geranylgeranyl pyrophosphate synthase in the presence of a polyaromatic resin to make a cell/resin mixture, wherein at least one of the cells further comprises at least one nucleic acid sequence of a yeast expression library, wherein the expression of the nucleic acid sequence is regulated by an inducible promoter and under conditions wherein the expression is induced; filtering the cell/resin mixture; extracting the cell/resin mixture with alcohol to produce an organic eluent; analyzing the organic eluent by a screening method, wherein the screening method is selected from the group consisting of chromatography, spectroscopy, or a combination thereof, and wherein the screening method identifies said diterpene synthase. A skilled artisan recognizes that yeast expression libraries are known, and methods to construct a yeast expression library are also known in the art and within the skill of a skilled artisan in the art. Furthermore, by the examples in Example 5, a skilled artisan is aware of methods to identify a diterpene synthase from processing of a cell/resin mixture include, for example, gas chromatography, gas chromatography/mass spectroscopy, and thin layer chromatography. Chromatography screens have been described by Corey et al. (1993).

Example 16

Summary of the Present Invention

Thus, in accordance with the objects of the present invention, there is an in vivo system for producing diterpenes and diterpene precursors. In a preferred embodiment, there is a yeast cell, wherein the yeast cell comprises a GGPP synthase such as BTS1, a soluble form of HMG-CoA reductase, and an allele that confers an increase in sterol metabolic flux, that produces exploitable amounts of diterpene precursor occurs in a cell, which does not naturally biosynthesize the increased amount of diterpene precursor.

In another preferred embodiment, there is a yeast cell, wherein the yeast cell comprises a GGPP synthase such as BTS1, a soluble form of HMG-CoA reductase, upc2-1 and a diterpene synthase that produces exploitable amounts of diterpene is produced in a cell, which does not naturally biosynthesize the diterpene. As described herein, hydrolysis of accumulating GGPP to GGOH has been observed in the compositions of the present invention. Diterpene production levels in vivo are a function of inducer concentration, metabolic flux, reaction rates of rate-limiting steps. Furthermore, diterpene and diterpene precursor yields are a function of the isolation and removal methods.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference herein.

Patents

U.S. Pat. No. 4,683,202 issued Jul. 28, 1987.
U.S. Pat. No. 4,879,236 issued Nov. 7, 1989.
U.S. Pat. No. 5,429,939 issued Jul. 4, 1995.
U.S. Pat. No. 5,589,581 issued Dec. 31, 1996.
U.S. Pat. No. 5,871,986 issued Feb. 16, 1999.
U.S. Pat. No. 5,925,565 issued Jul. 20, 1999.
U.S. Pat. No. 5,928,906 issued Jul. 27, 1999.
U.S. Pat. No. 5,935,819 issued Aug. 10, 1999.
EP Patent No. EP0393690 issued Oct. 24, 1990.
EP Patent No. EP0769551 issued Apr. 23, 1997.

PUBLICATIONS

Ausubel, F. M., Brent, R., Kingston, R. E., Moore, D. D., Seidman, J. G., Smith, J. A., Struhl, K. (1994). Current Protocols in Molecular Biology, John Wiley & Sons, Inc.

Bailey, J. E. (1991) Toward a Science of Metabolic Engineering. Science 252: 1668–1675.

Bask, K., Nah, J., Lee, S. B., Song, J. H., Shin, D. H., Kim, H. V. (2000) Mol Cells 10(2):220–225.

Basson, M. E., Thorsness, M., Rine, J. (1986) *Saccharomyces cerevisiae* contains two functional genes encoding 3-hydroxy-3-methylglutaryl-coenzyme A reductase. Proc. Natl. Acad. Sci. USA 83: 5563–67.

Basson, M. E., Moore, R. L., O'Rear, J., Rine, J. (1987) Identifying mutations in duplicated functions in *Saccharomyces cerevisiae*: recessive mutations in HMG-CoA reductase genes. Genetics 117: 645–655.

Bensen, R. J., Johal, G. S., Crane, V. C., Tossberg, J. T., Schnable, P. S., Meeley, R. B., Briggs, S. P. (1995) Plant Cell 7:75–84.

Bertolino, A., Altman, L. J., Vasak, J., Billing, H. C. (1978) Bioch. Biophys. Acta 530:17–23.

Bourot, S., Karst, F. (1995) Gene. 7:165(1):97–102.

Burke, D., Dawson, D., Stearns, T. (2000) Methods in Yeast Genetics, 2000 Edition: A Cold Spring Harbor Laboratory Course Manual, Cold Spring Harbor Laboratory, 205 pp.

Cherest, H., et al. (1985) Gene 34: 269–81.

Corey, E. J., Volante, R. P. (1976) J. Am. Chem. Soc. 98:1291–1293.

Corey E J, Matsuda S P, Bartel B. (1993) Isolation of an *Arabidopsis thaliana* gene encoding cycloartenol synthase by functional expression in a yeast mutant lacking lanosterol synthase by the use of a chromatographic screen. Proc Natl Acad Sci USA., 90(24):11628–32.

Epstein, W. W., Rilling, H. C. Studies on the mechanism of squalene biosynthesis. (1970) J. Biol. Chem. 245(18): 4597–4605.

Funk, C., Croteau, R. (1994) Arch. Biochem. Biophys. 308: 258–66.

Goldstein, J. L., Brown, M. S. Regulation of the mevalonate pathway. Nature 343: 425–430.

Hampton, et al. (1999) J. Biol. Chem. 274:31671–8.

Hara, M., Asano, K., Kawamoto, I., Takiguchi, T., Katsumata, S., Takahashi, K.-I., Nakao, H. (1989) J. Antibiotics 42:1768–1774.

Hill, A. M., Cane, D. E., Mau, J., West, C. A. (1996) Arch. Biochem. Biophys. 336:283–289.

Hottiger, T., Frst, P., Pohlig, G., Heim, J. (1994) Yeast 10: 283–296.

Jiang, Y, Proteau, P, Poulter, D, Ferro-Novick, S. BTS1 encodes a geranylgeranyl diphosphate synthase in *Saccharomyces cerevisiae*. (1995) J. Biol. Chem. 270 (37): 21793–21799.

Keller, R. K. Squalene synthase inhibition alters metabolism of nonsterols in rat liver. (1996) Bioch. Biophys. Acta 1303:169–179.

Leak, F. W., Tove, S., Parks, L. W. In yeast, upc2-1 confers a decrease in tolerance to LiCl and NaCl, which can be suppressed by the p-type ATPase encoded by ENA2. (1999) DNA Cell Biol. 18(2): 133–139.

Lewis T. L., Keesler G. A., Fenner G. P., Parks L. W. Pleiotropic mutations in *Saccharomyces cerevisiae* affecting sterol uptake and metabolism. (1988) Yeast 4(2):93–106.

Liu, S.-J., Steinbuchel, A. A novel genetically engineered pathway for synthesis of poly (hydroxyalkanoic acids) in *Escherichia coli*. (2000) Appl. Env. Microbiol. 66(2): 739–743.

Maniatis, T., Sambrook, J., Fritsch, E. F. (1989) Molecular Cloning: A Laboratory Manual, Cold Spring Harbor Laboratory.

Miura, Y, Kondo, K, Shimada, H, Saito, T, Nakamura, K, Misawa, N. Production of lycopene by the food yeast, *Candida utilis* that does not naturally synthesize carotenoid. (1998b) Biotech. Bioeng. 58(2, 3): 306–308.

Miura, Y., Kondo, K., Saito, T., Shimada, H., Fraser, P. D., Misawa, N. Production of the carotenoids lycopene, β-carotene, and astaxanthin in the food yeast *Candida utilis*. (1998a) Appl. Envir. Microbiol. 64(4): 1226–1229.

Mountain, H. A. et al. (1991) Yeast 7:781–803.

Ness F, Bourot S, Regnacq M, Spagnoli R, Berges T, Karst F. SUT1 is a putative Zn[II]2Cys6-transcription factor whose upregulation enhances both sterol uptake and synthesis in aerobically growing *Saccharomyces cerevisiae* cells. Eur J Biochem 2001 March;268(6):1585–95

Ortize de Montellano, P. R., Wei, J. S., Vinson, W. A., Castillo, R., Boparai, A. S. (1977) Biochemistry 16: 2680–2685.

Parks, L. W., Casey, W. M. Physiological implications of sterol biosynthesis in yeast. (1995) Annu. Rev. Microbiol. 49:95–116.

Parks, L. W., Smith, S. J., Crowley, J. H. Biochemical and physiological effects of sterol alterations in yeast-a review. (1995) Lipids 30(3): 227–230.

Paultauf, F., Kohlwein, S. D., Henry, S. A. (1992) Regulation and compartmentalization of lipid synthesis in yeast. In *The Molecular and Cellular Biology of the Yeast Saccharomyces: Gene Expression*. 2:415–500. Cold Spring Harbor, N.Y.: Cold Spring Harbor Lab.

Polakowski, T., Stahl, U., Lang, C. (1998) Appl. Microbiol. Biotechnol. 49: 66–71.

Poletti, A., Celotti, R., Motta, M., Martini, L. Biochem. J. 1996, 314, 1047–1052.

Popjak, G., Edmond, J., Clifford, K., Williams, V. (1969) Biosynthesis and structure of a new intermediate between farnesyl pyrophosphate and squalene. J. Biol. Chem. 244(7): 1897–1918.

Profant, D. A., Roberts, C. J., Koning, A. J., Wright, R. L. (1999) The role of the 3-hydroxy 3-methylglutaryl coenzyme A reductase cytosolic domain in karmellae biogenesis. Mol Biol Cell 10(10): 3409–23.

Rae, T. D., Schmidt, P. J., Pufahl, R. A., Culotta, V. C., O'Halloran, T. V. (1999) Science 284: 805–808.

Rilling, H. C. A new intermediate in the biosynthesis of squalene (1966) J. Biol. Chem. 241 (13):3233–3246.

Shimada, H., Kondo, K., Fraser, P. D., Miura, Y., Saito, T., Misawa, N. Increased carotenoid production by the food yeast *Candida utilis* through metabolic engineering of the isoprenoid pathway. (1998) Appl. Environ. Microbiol. 64(7): 2676–2680.

Stephanopolous, G. (2000) Bioinformatics and Metabolic Engineering. Metabol. Eng. 2(3): 157–158.

Stoffer-Vogel, B., Wildung, M. R., Vogel, G. (1996) J. Biol. Chem. 271: 23262–23268.

Sun, T.-P., Kamiya, Y. (1994) Plant Cell 6:1509–1518.

Wang, C.-W., Oh, M.-K., Liao, J. C., Engineered isoprenoid pathway enhances astaxanthin production in *Escherichia coli*. (1999) Biotech. Bioeng. 62(2): 235–308.

Yamaguchi, S., Saito, T., Abe, H., Yamane, H., Murofushi, N., Kamiya, T. (1996) Plant J. 10: 203–213.

Yamano, S., Ishii, T., Nakagawa, M., Ikenaga, H., Misawa, N. Metabolic engineering for production of β-carotene and lycopene in *Saccharomyces cerevisiae*. (1994) Biosci. Biotech. Biochem. 58 (6): 1112–1114.

One skilled in the art readily appreciates that the patent invention is well adapted to carry out the objectives and obtain the ends and advantages mentioned as well as those inherent therein. Yeast cells, cell cultures, sequences, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07238514B2). An electronic copy of the "Sequence Listing" will also be available from the USPTO upon request and payment of the fee set forth in 37 CFR 1.19(b)(3).

What is claimed:

1. A unicellular organism for producing a diterpene, comprising:
   a first exogenous nucleic acid having the sequence of SEQ ID NO: 1 and encoding a geranylgeranyl pyrophosphate synthase, the first nucleic acid under the control of a first promoter operable in said organism; and
   a second exogenous nucleic acid having the sequence of SEQ ID NO: 361 and encoding a diterpene synthase, the second nucleic acid under the control of a second promoter operable in said organism.

2. The unicellular organism of claim 1, wherein said first promoter comprises an inducible promoter or a constitutive promoter.

3. The unicellular organism of claim 2, wherein said inducible promoter is selected from the group consisting of GAL1, CUP1 and MET3.

4. The unicellular organism of claim 2, wherein said constitutive promoter is selected from the group consisting of alcohol dehydrogenase (ADH) promoter and phosphoglycerine kinase (PGK) promoter.

5. The unicellular organism of claim 1, wherein said second promoter comprises an inducible promoter or a constitutive promoter.

6. The unicellular organism of claim 5, wherein said inducible promoter is selected from the group consisting of GAL1, CUP1 and MET3.

7. The unicellular organism of claim 5, wherein said constitutive promoter is selected from the group consisting of alcohol dehydrogenase (ADH) promoter and phosphoglycerine kinase (PGK) promoter.

8. The unicellular organism of claim 1, wherein said unicellular organism further comprises a third exogenous nucleic acid encoding a soluble form of a 3-hydroxy-3-methyglutaryl-CoA reductase under control of a third promoter operable in said organism.

9. The unicellular organism of claim 8, wherein said third promoter comprises an inducible promoter or a constitutive promoter.

10. The unicellular organism of claim 9, wherein said inducible promoter is selected from the group consisting of GAL1, CUP1 and MET3.

11. The unicellular organism of claim 9, wherein said constitutive promoter is selected from the group consisting of alcohol dehydrogenase (ADH) promoter and phosphoglycerine kinase (PGK) promoter.

12. The unicellular organism of claim 8, wherein said unicellular organism further comprises a fourth exogenous nucleic acid having the sequence of SEQ ID NO: 399 under control of a fourth promoter operable in said organism.

13. The unicellular organism of claim 1, wherein said first nucleic acid encoding said geranylgeranyl pyrophosphate synthase is present on a chromosome of said unicellular organism.

14. The unicellular organism of claim 1, wherein said unicellular organism is a yeast.

15. The unicellular organism of claim 8, wherein said unicellular organism is a yeast.

16. The unicellular organism of claim 12, wherein said unicellular organism is a yeast.

17. A unicellular organism for producing a diterpene or diterpene precursor, comprising:
   a first exogenous polynucleotide encoding a geranylgeranyl pyrophosphate synthase having the amino acid sequence of SEQ ID NO: 22, the first polynucleotide under the control of a first promoter in said organism; and
   a second exogenous polynucleotide encoding a diterpene synthase having the amino acid sequence of SEQ ID NO: 383, the second polynucleotide under the control of a second promoter operable in said organism.

18. The unicellular organism of claim 17, wherein said organism is a yeast.

19. The unicellular organism of claim 8, wherein said unicellular organism further comprises a fourth exogenous nucleic acid encoding a sterol uptake control transcription factor under control of a fourth promoter operable in said organism.

20. The unicellular organism of claim 17, wherein said first promoter comprises an inducible promoter or a constitutive promoter.

21. The unicellular organism of claim 20, wherein said inducible promoter is selected from the group consisting of GAL1, CUP1 and MET3.

22. The unicellular organism of claim 20, wherein said constitutive promoter is selected from the group consisting of alcohol dehydrogenase (ADH) promoter and phosphoglycerine kinase (PGK) promoter.

23. The unicellular organism of claim 17, wherein said second promoter comprises an inducible promoter or a constitutive promoter.

24. The unicellular organism of claim 23, wherein said inducible promoter is selected from the group consisting of GAL1, CUP1 and MET3.

25. The unicellular organism of claim 23, wherein said constitutive promoter is selected from the group consisting of alcohol dehydrogenase (ADH) promoter and phosphoglycerine kinase (PGK) promoter.

26. The unicellular organism of claim 17, wherein said unicellular organism further comprises a third exogenous polynucleotide encoding a soluble form of 3-hydroxy-3-methyglutaryl-CoA reductase under control of a third promoter operable in said organism.

27. The unicellular organism of claim 26, wherein said third promoter comprises an inducible promoter or a constitutive promoter.

28. The unicellular organism of claim 27, wherein said inducible promoter is selected from the group consisting of GAL1, CUP1 and MET3.

29. The unicellular organism of claim 27, wherein said constitutive promoter is selected from the group consisting of alcohol dehydrogenase (ADH) promoter and phosphoglycerine kinase (PGK) promoter.

30. The unicellular organism of claim 26, wherein said unicellular organism further comprises a fourth exogenous polynucleotide having the sequence of SEQ ID NO: 399 and under control of a fourth promoter operable in said organism.

31. The unicellular organism of claim 26, wherein said unicellular organism further comprises a fourth exogenous polynucleotide encoding a sterol uptake control transcription factor under control of a fourth promoter operable in said organism.

32. The unicellular organism of claim 17, wherein said first polynucleotide encoding said geranylgeranyl pyrophosphate synthase is present on a chromosome of said unicellular organism.

33. The unicellular organism of claim 26, wherein said unicellular organism is a yeast.

34. The unicellular organism of claim 19, wherein said unicellular organism is a yeast.

35. The unicellular organism of claim 30, wherein said unicellular organism is a yeast.

36. The unicellular organism of claim 31, wherein said unicellular organism is a yeast.

37. The unicellular organism of claim 12, wherein said fourth nucleic acid and promoter are operable to confer to said organism an increase in sterol metabolic flux as compared to native sterol metabolic flux levels.

38. The unicellular organism of claim 19, wherein said fourth nucleic acid and promoter are operable to confer to said organism an increase in sterol metabolic flux as compared to native sterol metabolic flux levels.

39. The unicellular organism of claim 30, wherein said fourth polynucleotide and promoter are operable to confer to said organism an increase in sterol metabolic flux as compared to native sterol metabolic flux levels.

40. The unicellular organism of claim 31, wherein said fourth polynucleotide and promoter are operable to confer to said organism an increase in sterol metabolic flux as compared to native sterol metabolic flux levels.

41. The unicellular organism of claim 1, wherein said first exogenous nucleic acid and first promoter are contained in a vector.

42. The unicellular organism of claim 1, wherein said second exogenous nucleic acid and second promoter are contained in a vector.

43. The unicellular organism of claim 8, wherein said third exogenous nucleic acid and third promoter are contained in a vector.

44. The unicellular organism of claim 12, wherein said fourth exogenous nucleic acid and fourth promoter are contained in a vector.

45. The unicellular organism of claim 19, wherein said fourth exogenous nucleic acid and fourth promoter are contained in a vector.

46. The unicellular organism of claim 17, wherein said first exogenous polynucleotide and first promoter are contained in a vector.

47. The unicellular organism of claim 17, wherein said second exogenous polynucleotide and second promoter are contained in a vector.

48. The unicellular organism of claim 26, wherein said third exogenous polynucleotide and third promoter are contained in a vector.

49. The unicellular organism of claim 30, wherein said fourth exogenous polynucleotide and fourth promoter are contained in a vector.

50. The unicellular organism of claim 31, wherein said fourth exogenous polynucleotide and fourth promoter are contained in a vector.

51. The unicellular organism of claim 1, further comprising a first enhancer operable to enhance transcriptional activation of the first nucleic acid.

52. The unicellular organism of claim 51, further comprising a second enhancer operable to enhance transcriptional activation of the second nucleic acid.

53. The unicellular organism of claim 8, further comprising a first enhancer operable to enhance transcriptional activation of the first nucleic acid.

54. The unicellular organism of claim 53, further comprising a second enhancer operable to enhance transcriptional activation of the second nucleic acid.

55. The unicellular organism of claim 17, further comprising a first enhancer operable to enhance transcriptional activation of the first polynucleotide.

56. The unicellular organism of claim 55, further comprising a second enhancer operable to enhance transcriptional activation of the second polynucleotide.

57. The unicellular organism of claim 26, further comprising a first enhancer operable to enhance transcriptional activation of the first polynucleotide.

58. The unicellular organism of claim 57, further comprising a second enhancer operable to enhance transcriptional activation of the second polynucleotide.

59. The unicellular organism of claim 1, wherein the first and second promoters are the same promoter.

60. The unicellular organism of claim 8, wherein at least two of the first, second and third promoters are the same promoter.

61. The unicellular organism of claim 12, wherein at least two of the first, second, third and fourth promoters are the same promoter.

62. The unicellular organism of claim 19, wherein at least two of the first, second, third and fourth promoters are the same promoter.

63. The unicellular organism of claim 17, wherein the first and second promoters are the same promoter.

64. The unicellular organism of claim 26, wherein at least two of the first, second and third promoters are the same promoter.

65. The unicellular organism of claim 30, wherein at least two of the first, second, third and fourth promoters are the same promoter.

66. The unicellular organism of claim 31, wherein at least two of the first, second, third and fourth promoters are the same promoter.

67. The unicellular organism of claim 1, wherein a single exogenous nucleic acid comprises both the first and second exogenous nucleic acids.

68. The unicellular organism of claim 67, wherein the single exogenous nucleic acid comprises at least one internal ribosome binding site.

69. The unicellular organism of claim 17, wherein a single exogenous polynucleotide comprises both the first and second exogenous polynucleotides.

* * * * *